United States Patent
McCord et al.

(10) Patent No.: US 6,190,658 B1
(45) Date of Patent: Feb. 20, 2001

(54) GENETICALLY MODIFIED MANGANESE SUPEROXIDE DISMUTASE FOR TREATING OXIDATIVE DAMAGE

(75) Inventors: Joe M. McCord; Bifeng Gao, both of Denver; Sonia C. Flores, Parker, all of CO (US)

(73) Assignee: Webb-Waring Institute for Biomedical Research, Denver, CO (US)

(*) Notice: Under 35 U.S.C. 154(b), the term of this patent shall be extended for 0 days.

(21) Appl. No.: 09/075,019

(22) Filed: May 8, 1998

(51) Int. Cl.[7] .............................. A61K 38/44; C12Q 1/68; C12N 9/02
(52) U.S. Cl. ...................... 424/94.4; 435/6; 435/189
(58) Field of Search .................. 435/6, 189, 320.1, 435/325, 252.3; 424/94.4; 536/23.2

(56) References Cited

U.S. PATENT DOCUMENTS

| | | | |
|---|---|---|---|
| 5,227,405 | 7/1993 | Fridovich et al. | 514/612 |
| 5,238,837 | 8/1993 | Inoue et al. | 435/189 |
| 5,270,195 | 12/1993 | Hartman et al. | 435/189 |
| 5,342,921 | 8/1994 | Cousens et al. | 530/324 |
| 5,366,729 | 11/1994 | Marklund et al. | 424/94.4 |
| 5,403,731 | 4/1995 | Nakano et al. | 435/181 |
| 5,455,029 | 10/1995 | Hartman et al. | 424/94.4 |
| 5,472,691 | 12/1995 | Marklund et al. | 424/94.4 |
| 5,525,463 | 6/1996 | Zolg | 435/6 |
| 5,540,911 | 7/1996 | Hartman et al. | 424/94.4 |
| 5,589,371 | 12/1996 | Heckl et al. | 435/189 |
| 5,629,189 | 5/1997 | Hallewell et al. | 435/189 |
| 5,637,578 | 6/1997 | Riley et al. | 514/186 |
| 5,670,371 | 9/1997 | Aviv et al. | 435/320.1 |
| 5,691,139 | 11/1997 | Hallewell et al. | 435/6 |
| 5,710,033 | 1/1998 | Hallewell et al. | 435/189 |
| 5,843,641 | * 12/1998 | Brown et al. | 435/6 |
| 5,849,290 | 12/1998 | Brown et al. | 424/94.4 |

FOREIGN PATENT DOCUMENTS

WO 90/10694  9/1990  (WO).
WO 94/19493  9/1994  (WO).

OTHER PUBLICATIONS

GenBank Accession No. X03951.
GenBank Accession No. M77690.
GenBank Accession No. M77789.
Gao et al., Gene, 176:269–272 (1996).
Inoue et al., FEBS Letters, 269, 89–92, Aug. 1990.*
Giglio et al., "The Manganese Superoxide Dismutase Gene of Caenorhabditis Elegans", Biochemistry and Molecular Biology Internartional, vol. 33, No., 1, May 1999, pp. 37–40.
Serebriiskii et al. "Two new members of the Bio B superfamily: cloning, sequencing and expression of bioB genes of *Methylobacillus flagellatum* and *Corynebacterium glutamicum*", Gene 175, 1996, pp. 15–22.
Liu et al., "Transfection and Expression of MnSOD cDNA Decreases Tumor Malignancy of Human Oral Squamous Carcinoma SCC–25 Cells", Human Gene Therapy, Mar. 20, 1997, vol. 8, pp. 585–595.
Simonson et al., "Aerosolized manganese SOD decrease hyperoxic pulmonary injury in primates. I. Physiology and biochemistry", J. App. Physiol, 1997, vol. 83, pp. 550–558.
Ho et al., "Isolation and characterization of complementary DNAs encoding human maganese–containing superoxide dismutase", FEBS Letter, Mar. 1998, vol. 229, No. 2, pp. 256–260.

* cited by examiner

*Primary Examiner*—Rebecca E. Prouty
*Assistant Examiner*—M Monshipouri
(74) *Attorney, Agent, or Firm*—Sheridan Ross P.C.

(57) ABSTRACT

This invention discloses a genetically modified manganese superoxide dismutase nucleic acid molecule and protein. Also disclosed are recombinant molecules, recombinant cells, therapeutic compositions and methods of using the modified manganese superoxide dismutase to treat oxidative damage.

23 Claims, 10 Drawing Sheets

GENETICALLY MODIFIED MANGANESE SUPEROXIDE DISMUTASE FOR TREATING OXIDATIVE DAMAGE

GOVERNMENT RIGHTS

This invention was made in part with government support under NIH HL-40784, awarded by the National Institutes of Health. The government has certain rights to this invention.

FIELD OF THE INVENTION

The present invention generally relates to a genetically modified superoxide dismutase enzyme and methods for treating oxidative damage by administration of such an enzyme.

BACKGROUND OF THE INVENTION

Active oxygen species are involved in the pathogenesis of a variety of diseases. Accumulation of active oxygen species, and oxygen-free radicals, as well as direct oxygen toxicity can cause oxidative damage to cells. Oxidative damage can occur in various lung diseases, cancer and inflammatory diseases, and in other conditions involving hypoxia or ischemia-reperfusion injury, such as organ transplantation.

In many laboratory models and in a few clinical trials, superoxide dismutase (SOD) has proven therapeutically useful in protecting injured tissues from one of these active oxygen species, the superoxide radical (McCord et al., Superoxide production and human disease, 1992, *Molecular Basis of Oxidative Damage by Leukocytes*, Boca Raton: CRC Press, pp. 225–239; Delanian et al., 1994, *Radiother. Oncol.* 32:12–20; Sanchiz et al., 1996, *Anticancer. Res.* 16:2025–2028). Other enzymes which are part of the cell's arsenal against these active oxygen species include catalase and glutathione peroxidase, which eliminate $H_2O_2$. The ability of SOD to protect tissues against any particular insult (ischemia, inflammation, hyperoxia, etc.), however, depends on several parameters, such as its rate of plasma clearance, its ability to equilibrate between extracellular fluid compartments, and its ability to closely approach negatively-charged cell surfaces.

In humans, three isozymes of SOD have been extensively characterized: the cytosolic cuprozinc SOD (Cu,ZnSOD), a 32 kDa dimer; the mitochondrial manganese SOD (MnSOD), an 89 kDa tetramer; and an extracellular SOD (ECSOD), a 135 kDa tetrameric glycoprotein which is also a cuprozinc enzyme. ECSOD is genetically related to the smaller cytosolic enzyme, Cu,ZnSOD, and is found in a number of tissues but at a much lower concentration than either of the other two enzymes. It is, however, the major SOD in extracellular fluids. Plasma membranes of endothelial and parenchymal cells of various tissues are often exposed to the superoxide radical generated by activated phagocytes, and are partially protected from this oxidative attack by an extracellular superoxide dismutase (ECSOD) electrostatically bound to their surfaces. ECSOD is found as three different forms: ECSOD-A with no heparin affinity, ECSOD-B with low heparin affinity, and ECSOD-C with high heparin affinity. Sandstrom et al. (1992, *J. Biol. Chem.* 267:18205–18209) have suggested that forms A and B are generated by proteolytic cleavage of a carboxyl-terminal "tail" found on ECSOD-C. The highly hydrophilic positively charged nature of this carboxyl-terminal "tail" imparts the high heparin affinity which allows the enzyme to be largely bound to heparan sulfate on endothelial surfaces.

Under normal physiological circumstances, intracellularly generated superoxide is efficiently handled by the cytosolic Cu,ZnSOD and mitochondrial MnSOD. However, under pathological conditions, large amounts of superoxide and its metabolites are produced extracellularly by activated neutrophils and other phagocytic cells. In this case, one major site of oxidant attack is endothelial cell surfaces, where membrane perturbation leading to cell death (possibly through apoptosis or programmed cell death) may be induced. Therefore, it seems clear that the plasma membranes of vascular endothelial cells and parenchymal cells should be protected when there is excessive production of these species. Surface-bound ECSOD-C normally protects endothelial cell surfaces from superoxide attack. However, proteases released by inflammatory cells may cleave the ECSOD "tail" allowing the enzyme to become soluble and rendering the endothelium susceptible to superoxide attack.

To protect the endothelium, most therapeutic efforts prior to the present invention have attempted to utilize the cytosolic Cu,ZnSOD, which unfortunately has undesirable pharmacological properties, including a short plasma half life following intravenous (i.v.) injection (6 to 15 minutes, depending on species), with rapid clearance by the kidneys, and a net negative charge at physiologic pH. This net negative charge precludes close contact with cellular surfaces and/or movement into interstitial spaces. In contrast, MnSOD is positively charged at physiologic pH and has a longer plasma half-life of about 4 hours. In an isolated perfused heart model, MnSOD equilibrates more quickly than the native Cu,ZnSOD and is more protective (Omar et al., 1991, *J. Mol. Cell Cardiol.*, 23:149–159; incorporated by reference herein in its entirety). ECSOD, however, may have a substantial advantage over both Cu,ZnSOD and MnSOD because of its ability to bind to the endothelium. Recombinant ECSOD, however, has been produced only in a low-yield mammalian cell culture system (Tibell et al., 1987, *Proc. Natl. Acad. Sci. USA*, 84:6634–6638). All attempts to express this protein in a bacterial high-expression system have failed.

Moreover, while recombinant human ECSOD was found to be cardioprotective in the isolated rat heart subjected to ischemia and reperfusion, the effects noted by Sjöquist et al. "were essentially the same as those observed in hearts perfused with bovine Cu,ZnSOD" (Sjöquist et al., 1991, *J. Cardiovasc. Pharmacol.* 17:678–683), although Pisarenko et al. found ECSOD somewhat more than twice as effective as bovine Cu,ZnSOD (Pisarenko et al., 1994, *J.Cardiovasc.Pharmacol.* 24:655–663). In a similar study that used a spin-trapping agent to assess free radical production, the ECSOD was found to reduce free radical concentrations "at least to the same extent as Cu—Zn superoxide dismutase" (Johansson et al., 1990, *Cardiovasc.Res.* 24:500–503). Abrahamsson et al. (1992, *Circ.Res.* 70:264–271) used pyrogallol to generate superoxide radicals in a bath containing rabbit aorta rings. The free radical exposure inhibited the rings' ability to relax when acetylcholine was added to the bath, and this effect could be blocked by SOD added to the bath. Surprisingly, ECSOD produced a dose-response curve identical to that seen with Cu,ZnSOD. However, when the rings were pretreated with SOD, then washed, and then exposed to the radical-generating systeir. followed by acetylcholine, ECSOD showed its ability to "stick" and provide a degree of protection even after washing. The protection provided by Cu,ZnSOD was effectively all washed away. All in all, ECSOD has been rather disappointing in its ability to protect tissues from radical-mediated injury, being only marginally better than Cu,ZnSOD.

Inoue et al. (1990, *FEBS Lett.* 269:89–92) have attempted to improve the properties of Cu,ZnSOD by genetic engineering. They created a fusion gene consisting essentially of the cDNA encoding human Cu,ZnSOD fused to a synthetic oligonucleotide region that adds C-terminal amino acids of human ECSOD. This mutant is called HB-SOD, because it has heparin-binding properties similar to ECSOD. Functionally, the HB-SOD is superior to native Cu,ZnSOD in some models, but not in others. In the spontaneously hypertensive rat HB-SOD lowered the blood pressure, whereas native Cu,ZnSOD at the same dosage had no effect at all (Nakazono et al., 1991, *Proc. Natl. Acad. Sci. USA* 88:10045–10048). In carrageenan-induced foot edema in the rat, however, HB-SOD and native Cu,ZnSOD had the same relative effect (Oyanagui et al., 1991, *Biochem.Pharmacol.* 42:991–995).

Therefore, although much work in the past three decades has attempted to utilize SOD as a therapeutic agent, with most of the effort being focused on the cytosolic SODs, while there have been successes under laboratory conditions where dosing and clearance may be carefully controlled, very little of this success has found its way into clinical application where the picture becomes more complex. Moreover, many of the recombinant SOD agents have been difficult to produce in useful quantities. Thus, there remains a need in the art for a therapeutic agent having the properties of a superoxide dismutase, which is effective both in the laboratory and for in vivo treatment of oxidative damage in a variety of conditions, and which can be expressed easily and economically in a high-yield expression system.

SUMMARY OF THE INVENTION

One embodiment of the present invention relates to an isolated nucleic acid molecule which comprises: (a) a first nucleic acid sequence encoding a protein which includes an enzymatically active portion of manganese superoxide dismutase (MnSOD); and (b) a second nucleic acid molecule which encodes a peptide that binds to polyanionic polysaccharides or proteoglycans on endothelial cell surfaces. The first and second nucleic acid sequences can be arranged in any order on the isolated nucleic acid molecule. In one embodiment, the first nucleic acid sequence is positioned 5' of the second nucleic acid sequence, such that the protein which includes an enzymatically active portion of MnSOD is expressed N-terminal to the peptide that binds to polyanionic polysaccharides or proteoglycans. In another embodiment, the second nucleic acid sequence is positioned 5' of the first nucleic acid sequence, such that the peptide that binds to polyanionic polysaccharides or proteoglycans is expressed N-terminal to the protein which includes an enzymatically active portion of MnSOD.

The first nucleic acid sequence, in one embodiment, encodes a protein comprising the enzymatically active portion of human MnSOD. In another embodiment, the first nucleic acid sequence encodes human MnSOD or a naturally occurring allelic variant thereof. In yet another embodiment, the first nucleic acid sequence comprises SEQ ID NO:1.

The second nucleic acid sequence, in one embodiment, encodes a peptide having an amino acid sequence which includes: (a) at least about five positively charged amino acid residues within a ten-residue region of the amino acid sequence selected from lysine and/or arginine; and, (b) at least about two amino acid residues poorly hydrolyzable by human plasma carboxypeptidases which are positioned at an end of said amino acid sequence. Such poorly hydrolyzable residues can be selected from the group of proline, alanine, and leucine.

In another embodiment, the second nucleic acid sequence encodes a peptide which includes the portion of extracellular superoxide dismutase C (ECSOD-C) which binds to heparin. In yet another embodiment, the second nucleic acid sequence encodes a peptide comprising the C-terminal region of ECSOD-C or a naturally occurring allelic variant thereof, and in another embodiment, the second nucleic acid sequence is SEQ ID NO:4.

The isolated nucleic acid sequence of the present invention, in one embodiment, hybridizes under stringent hybridization conditions to a nucleic acid molecule selected from: (a) a nucleic acid molecule comprising both nucleic acid sequences SEQ ID NO:1 and SEQ ID NO:4; (b) a nucleic acid molecule comprising a nucleic acid sequence SEQ ID NO:6; or (c) a nucleic acid molecule comprising a nucleic acid sequence SEQ ID NO:8. In another embodiment, an isolated nucleic acid molecule of the present invention comprises a nucleic acid molecule selected from: (a) a nucleic acid molecule comprising both nucleic acid sequences SEQ ID NO:1 and SEQ ID NO:4; (b) a nucleic acid molecule comprising a nucleic acid sequence SEQ ID NO:6; or (c) a nucleic acid molecule comprising a nucleic acid sequence SEQ ID NO:8. In yet another embodiment, an isolated nucleic acid molecule of the present invention hybridizes under stringent hybridization conditions to nucleic acid molecule pGB1MMN. In another embodiment, an isolated nucleic acid molecule of the present invention comprises nucleic acid molecule pGB1MMN.

An isolated nucleic acid molecule of the present invention preferably encodes a protein which binds to polyanionic polysaccharides or proteoglycans on endothelial cell surfaces. Such polyanionic polysaccharides or proteoglycans include, but are not limited to, heparin and heparan sulfate.

In another embodiment, an isolated nucleic acid molecule of the present invention preferably encodes a protein that protects a mammal from oxidative damage. In yet another embodiment, such protein protects a mammal from a condition which includes pulmonary inflammatory injury, lung disease, cancer, hypoxia, ischemia reperfusion injury, hyperoxia, atherosclerosis, arthritis, lupus erythematosus, hypertension and/or neutrophil-mediated inflammation.

Another embodiment of the present invention relates to an isolated recombinant molecule comprising an isolated nucleic acid molecule as set forth above that is operatively linked to a transcription control sequence. Yet another embodiment relates to a recombinant cell comprising the isolated nucleic acid molecule as set forth above, wherein the recombinant cell expresses the nucleic acid molecule.

Yet another embodiment of the present invention relates to an isolated mutant manganese superoxide dismutase (mut-MnSOD) protein. Such protein comprises an enzymatically active portion of MnSOD and a region which binds to polyanionic polysaccharides or proteoglycans on endothelial cell surfaces. In one embodiment, the region which binds to polyanionic polysaccharides or proteoglycans is located at the C-terminus of the isolated protein. In a preferred embodiment, the isolated mut-MnSOD protein, when administered to a mammal, protects the mammal from oxidative damage.

In one embodiment, the isolated mut-MnSOD protein is encoded by an isolated nucleic acid molecule as set forth in various embodiments above. In another embodiment, the isolated mut-MnSOD protein comprises an amino acid sequence selected from: (a) an amino acid sequence comprising both SEQ ID NO:2 and SEQ ID NO:5; (b) an amino acid sequence comprising SEQ ID NO:7; (c) an amino acid sequence that differs from the amino acid sequence comprising both SEQ ID NO:2 and SEQ ID NO:5 by one or a few amino acid insertions, deletions or substitutions that do not substantially affect MnSOD enzymatic activity of the isolated protein or the ability of the isolated protein to bind to polyanionic polysaccharides or proteoglycans; or (d) an amino acid sequence that differs from SEQ ID NO:7 by one or a few amino acid insertions, deletions or substitutions that do not substantially affect the MnSOD enzymatic activity of the isolated protein or the ability of the isolated protein to bind to polyanionic polysaccharides or proteoglycans. In one embodiment, the isolated mut-MnSOD protein comprises a fusion segment.

Another embodiment of the present invention relates to an antibody that selectively binds to the isolated mut-MnSOD protein as set forth in the various embodiments above.

Yet another embodiment of the present invention relates to a therapeutic composition to protect a mammal from oxidative damage. Such a therapeutic composition includes: (a) a protective compound which can be (i) an isolated mutant MnSOD protein as set forth above; or (ii) an isolated nucleic acid molecule as set forth above; and (b) a pharmaceutically acceptable delivery vehicle. A pharmaceutically acceptable vehicle can include, but is not limited to liposomes, recombinant cells, biocompatible polymers, other polymeric matrices, capsules, microcapsules, microparticles, bolus preparations, osmotic pumps, diffusion devices, liposheres, transdermal delivery systems, and/or surfactants.

Another embodiment of the present invention relates to an isolated recombinant nucleic acid molecule which comprises: (a) a nucleic acid sequence encoding a PsodA promoter and Shine-Dalgarno sequence of E. coli manganese superoxide dismutase (MnSOD); (b) an ATG translation initiation codon; (c) a nucleic acid sequence encoding human MnSOD; (d) a nucleic acid sequence encoding a C-terminal region of human extracellular superoxide dismutase; (e) a nucleic acid sequence encoding a transcription termination signal of E. coli MnSOD; and, (f) a nucleic acid sequence comprising a bacterial origin of replication sequence.

Yet another embodiment of the present invention relates to a method to produce a mutant MnSOD protein of the present invention as set forth above. Such method includes the step of culturing in an effective medium a recombinant cell capable of expressing the mut-MnSOD protein, wherein such cell comprises a nucleic acid molecule of the present invention as set forth above.

Another embodiment of the present invention relates to a method to protect a mammal from oxidative damage, which includes administering to a mammal a mutant manganese superoxide dismutase (MnSOD) protein comprising an enzymatically active portion of MnSOD and a C-terminal region which binds to polyanionic polysaccharides or proteoglycans on endothelial cell surfaces as set forth above. Such method can be used in a mammal which has a condition which includes, but is not limited to, pulmonary inflammatory injury, lung disease, cancer, hypoxia, ischemia reperfusion injury, hyperoxia, atherosclerosis, arthritis, lupus erythematosus, hypertension and/or neutrophil-mediated inflammation. A lung disease can further include, but is not limited to infant respiratory distress syndrome, adult respiratory distress syndrome, interstitial lung disease and asthma.

In the method of the present invention, a mutant manganese superoxide dismutase (mut-MnSOD) protein can be administered by at least one route which includes, but is not limited to oral, nasal, intratracheal, inhaled, transdermal, rectal and parenteral routes. In one embodiment, the mut-MnSOD is administered in a pharmaceutically acceptable delivery vehicle. The protein can be administered in an amount that is between about 50 U/kg and 15,000 U/kg body weight of the mammal.

In one embodiment of the method of the present invention, administration of the mut-MnSOD to a mammal results in the binding of the protein to endothelial cell surfaces in the mammal. In another embodiment, administration of the mut-MnSOD protects the mammal from oxidative damage. In yet another embodiment, administration of the mut-MnSOD protects the mammal from acute lung injury due to oxidative damage. In another embodiment, administration of the mut-MnSOD reduces neutrophil-mediated inflammation in the mammal. In yet another embodiment, administration of the mut-MnSOD to organe of the mammal protects the organs from pre-transplantation and/or post-transplantation oxidative damage. In a preferred embodiment, the mammal to which mut-MnSOD is administered is a human.

BRIEF DESCRIPTION OF THE FIGURES OF THE INVENTION

DETAILED DESCRIPTION OF THE INVENTION

The present invention generally relates to a genetically-engineered recombinant superoxide dismutase (SOD) with optimized pharmacological properties. To provide a therapeutic supplementation of the natural protection afforded tissues by endogenous SODs, the present inventors have constructed a genetically engineered SOD that incorporates desirable features of the mitochondrial manganese superoxide dismutase (MnSOD), together with a moiety which binds to polyanionic polysaccharides or proteoglycans on endothelial cell surfaces, such as heparin and heparan sulfate. This genetically engineered SOD of the present invention is generally referred to herein as mutant MnSOD, or mut-MnSOD. More specifically, the mutant SOD of the present invention has desirable characteristics of mature human MnSOD which include MnSOD enzymatic activity, the ability to extravasate quickly (i.e., pass into tissues quickly), the ability to resist renal clearance, and lack of interference with the bactericidal action of phagocytes, these characteristics being combined with the above described endothelial cell binding ability, such binding ability being characteristic of extracellular superoxide dismutase-C (ECSOD-C), for example.

As a therapeutic agent, the properties of the mutant MnSOD of the present invention are superior to those of any of the three naturally occurring human SODs, or to any genetically-engineered version of any SOD for which comparable data are available. In addition, to obtain high level expression of the novel mutant enzyme of the present invention, the present inventors have designed and constructed a novel expression vector which enables highly efficient and economical expression of the mutant MnSOD of the present invention.

The mutant MnSOD of the present invention, unlike any naturally occurring SOD or previously described genetically engineered SOD, has the following five identifying characteristics:

1) it binds to extracellular surfaces;
2) it extravasates quickly, reflecting its net charge;
3) it resists renal clearance;
4) it does not interfere with the bactericidal action of phagocytes; and,
5) it is able to be expressed easily and economically in a high-yield expression system.

As discussed above, prior to the present invention, many investigators have attempted to utilize SOD, including both native and genetically modified SODs, as a therapeutic agent, with most of the effort being focused on the cytosolic SODS (i.e., Cu,ZnSOD). These attempts have met with very little success in clinical applications.

Figure 15:
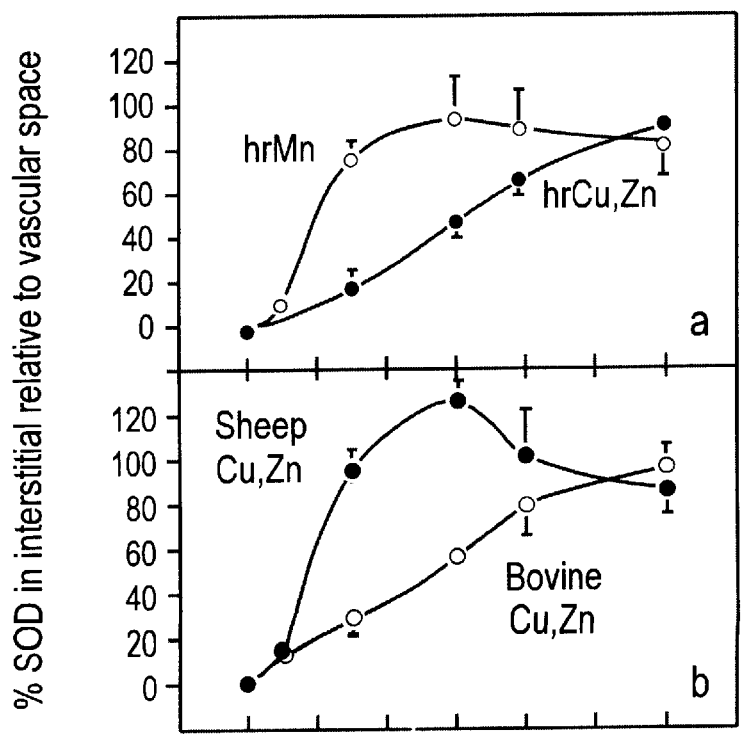
FIGS. 15a–15b is a line graph illustrating the time course for the appearance of SOD activity in the interstitial space of an isolated rabbit heart relative to that being perfused through the vascular compartment.

Native human Cu,ZnSOD, which has been by far the most widely used SOD in both laboratory and clinical trials, fails to demonstrate the first three characteristics set forth above. FIG. 15 (See Example 9) shows how the strongly negatively charged human and bovine Cu,ZnSODs equilibrate slowly from vascular space to interstitial space. It has been previously shown (Omar et al., 1991, supra) that protection of the reperfused myocardium correlates with the concentration of SOD in the interstitium, not in the vasculature.

Despite its higher molecular weight of 88 kDa (vs. 32 kDa for the native Cu,ZnSOD), native human MnSOD extravasates about four-fold faster than the Cu,ZnSOD as shown in FIG. 15. Its slower plasma clearance rate permits much easier maintenance of proper dosages in vivo, relative to the rapidly cleared Cu,ZnSOD. Native MnSOD satisfies the above-described identifying characteristics 2, 3, 4 and 5, but is lacking in the first characteristic of the ability to bind to extracellular surfaces by polyanionic polysaccharides or proteoglycans (also referred to herein as heparin-binding ability). The importance of this first characteristic of the novel SOD of the present invention is demonstrated herein by the efficacy obtained with this molecule as described in detail in the Examples section.

As discussed above, recombinant human ECSOD has been produced in relatively low yield in a Chinese hamster ovary cell expression system (Tibell et al., supra). Many laboratories have attempted to express this gene in high-yield bacterial or yeast systems without success. The reason for this difficulty is not entirely clear, but is probably related to the unusually high G-C content of the gene. In any event, native human ECSOD fails to meet characteristic 5 above, even though it has some strength in characteristics 1, 3 and 4. Its rate of extravasation is not known, but because its net charge is intermediate between Cu,ZnSOD and MnSOD (see FIG. 14) it may be expected to have an intermediate rate of extravasation as well. Nonetheless, the inability of recombinant ECSOD to protect tissues from oxidative damage has been disappointing, as discussed above in detail.

Finally, attempts to improve the properties of native Cu,ZnSOD have been made by genetically engineering the molecule to contain the cytoplasmic tail of ECSOD (See HB-SOD, Inoue et al., supra). As discussed above, functionally, the HB-SOD has been disappointing, because although it is superior to native Cu,ZnSOD in some models, in other models, it does not perform better than native Cu,ZnSOD. In view of the limited success of the HB-SOD, as discussed above, it is unexpected that an MnSOD having the cytoplasmic tail of ECSOD would perform significantly better than the genetically engineered Cu,ZnSOD, HB-SOD. The present inventors have discovered, however, that the genetically modified Cu,ZnSOD differs from the mutant MnSOD (mut-MnSOD) of the present invention in several potentially important ways. The mutant SOD, HB-SOD, has extracellular binding properties similar to ECSOD, and therefore has the first identifying characteristic set forth above, but like native Cu,ZnSOD, HB-SOD does not have the second and third characteristic of the mutant-MnSOD of the present invention. Moreover, the net charge of HB-SOD at pH 7.4 is −1.2, compared to a net charge of +3.1 for the mut-MnSOD. Since its parent SOD is dimeric, HB-SOD has two heparin-binding regions (e.g., polyanionic polysaccharide or proteoglycan-binding regions) per molecule, whereas the mut-MnSOD has four. Without being bound by theory, the present inventors believe that the tetrameric binding properties of the mut-MnSOD may contribute to the superior efficacy of the mut-MnSOD compared to HB-SOD. Carlsson et al. (1996, *Proc. Natl. Acad. Sci. U.S.A.* 93:5219–5222) have shown that rat and mouse ECSODs exist as dimers if aspartate is at position 28 and as tetramers if valine is in this position. The tetrameric enzymes have much higher affinity for heparin-binding than the corresponding dimeric enzymes, causing these authors to conclude that "the cooperative action of four heparin binding domains is necessary for high heparin affinity."

As discussed above, as a therapeutic agent, the mut-MnSOD of the present invention is superior to any native SOD or genetically engineered SOD for which comparable data is available. A comparison of mut-MnSOD with the most structurally similar genetically engineered SOD, HB-SOD, illustrates this point. In the spontaneously hypertensive rat, HB-SOD lowered blood pressure by about 50 mmHg 10 minutes after injection at a dosage of 25 mg/kg (or 69,000 U/kg), whereas native Cu,ZnSOD at the same dosage had no effect at all, initially suggesting that HB-SOD was more efficacious than the native SOD (Nakazono et al., 1991, *Proc. Natl. Acad. Sci. USA* 88:10045–10048). In carrageenan-induced foot edema in the rat, however, HB-SOD and native Cu,ZnSOD had the same $ED_{30}$ of 2,500 U/kg (Oyanagui et al., 1991, *Biochem. Pharmacol.* 42:991–995). In a comparative experiment, FIG. 13 (See Example 7) shows that mut-MnSOD has an $ED_{30}$ in this foot edema model of <100 U/kg, while native MnSOD at the same dose produced no significant suppression of edema. Thus, even though HB-SOD and mut-MnSOD have some structural and functional similarities, mut-MnSOD is 25-fold more effective than HB-SOD in the foot edema model. The functional superiority of the mut-MnSOD of the present invention will be described in more detail below.

One embodiment of the present invention relates to an isolated nucleic acid molecule comprising: (a) a first nucleic acid sequence encoding a protein comprising an enzymatically active portion of manganese superoxide dismutase (MnSOD); and, (b) a second nucleic acid sequence encoding a peptide that binds to polyanionic polysaccharides or proteoglycans on endothelial cell surfaces. Such a nucleic acid molecule encodes a mut-MnSOD of the present invention which has all five of the identifying characteristics as outlined above. Its success as a therapeutic agent exceeds the three naturally occurring forms of human SOD in a variety of models, and exceeds as well the success of other genetically-engineered variants of SOD. Unlike true ECSOD, the engineered enzyme of the present invention is readily expressed at very high levels in *E. coli*, and is easily purified to homogeneity by a simple procedure utilizing its heparin affinity.

In accordance with the present invention, an isolated nucleic acid molecule is a nucleic acid molecule that has beer removed from its natural milieu (i.e., that has been subject to human manipulation) and can include DNA, RNA, or derivatives of either DNA or RNA. As such, "isolated" does not reflect the extent to which the nucleic acid molecule has been purified. An isolated mutant MnSOD nucleic acid molecule of the present invention is produced using recombinant DNA technology (e.g., polymerase chain reaction (PCR) amplification, cloning) or chemical synthesis. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a mutant-MnSOD protein of the present invention.

The first and second nucleic acid sequences included within the isolated nucleic acid molecule of the present invention can be positioned within the nucleic acid molecule in any order, without affecting the ability of the protein encoded by the nucleic acid molecule to bind to endothelial cell surfaces or to be enzymatically active. In one embodiment, the first nucleic acid sequence encoding a protein comprising an enzymatically active portion of MnSOD is positioned (i.e., located) 5' of the second nucleic acid sequence encoding a peptide that binds to polyanionic polysaccharides or proteoglycans on endothelial cell surfaces. In this embodiment, when the isolated nucleic acid molecule is expressed, the protein comprising the enzymatically active portion of MnSOD is located) N-terminal of the peptide that binds to polyanionic polysaccharides or proteoglycans. In another embodiment, the second nucleic acid sequence encoding the endothelial cell binding peptide is positioned 5' of the first nucleic acid molecule encoding a protein comprising an enzymatically active portion of MnSOD. In this embodiment, when the isolated nucleic acid molecule is expressed, the peptide that binds to polyanionic polysaccharides or proteoglycans is located N-terminal to the protein comprising an enzymatically active portion of MnSOD.

According to the present invention, an enzymatically active portion of manganese superoxide dismutase (MnSOD) refers to a protein having an amino acid sequence that is sufficiently identical to a portion of a naturally occurring (i.e., native or endogenous) manganese superoxide dismutase protein such that the portion confers upon the mutant-MnSOD protein substantially the same enzymatic activity as the native MnSOD protein. Native MnSOD enzymatic activity can be determined by methods known to those of skill in the art. See for example, McCord et al., 1969, *J. Biol. Chem.* 244:6049–6055, which is incorporated herein by reference in its entirety. According to the present invention, an enzymatically active portion of MnSOD refers to a portion of an MnSOD protein, or a homologue thereof, that has a specific activity of at least about 600 U/mg, and more preferably, at least about 1500 U/mg, and even more preferably, at least about 3000 U/mg, as determined by standard methods of measuring MnSOD activity known in the art (for example, McCord et al., supra).

An enzymatically active portion of MnSOD need not necessarily comprise a consecutive amino acid sequence of a given region of native MnSOD, but rather, it need only comprise residues of native MnSOD which preserve the enzymatic activity of the given region of MnSOD, as set forth above. Therefore, it is within the scope of the present invention to modify one or a few nucleotides within the nucleic acid sequence encoding an enzymatically active portion of MnSOD by, for example, addition, deletion, and/or substitution of nucleotides, as long as the protein encoded by such sequence maintains substantially the same enzymatic activity as an endogenous MnSOD.

Accordingly, an enzymatically active portion of MnSOD can be a full-length MnSOD protein, an enzymatically active portion of a full-length MnSOD protein, or any homologue of such proteins, such as an MnSOD protein in which at least one or a few amino acids have been deleted (e.g., a truncatec version of the protein, such as a peptide), inserted, inverted, substituted and/or derivatized (e.g., by glycosylation, phosphorylation, acetylation, myristoylation, prenylation, palmitation, amidation and/or addition of glycosylphosphatidyl inositol). A homologue of an MnSOD protein is a protein having an amino acid sequence that is sufficiently similar to a native (i.e., naturally occurring, endogenous or wild-type) MnSOD protein amino acid sequence that a nucleic acid sequence encoding the homologue is capable of hybridizing under stringent conditions to (i.e., with) a nucleic acid molecule encoding the natural MnSOD protein (i.e., to the complement of the nucleic acid strand encoding the natural MnSOD protein amino acid sequence). A nucleic acid sequence complement of any nucleic acid sequence of the present invention refers to the nucleic acid sequence of the nucleic acid strand that is complementary to (i.e., can form a complete double helix with) the strand for which the sequence is cited. It is to be noted that a double-stranded nucleic acid molecule of the present invention for which a nucleic acid sequence has been determined for one strand that is represented by a SEQ ID NO also comprises a complementary strand having a sequence that is a complement of that SEQ ID NO. As such, nucleic acid molecules of the present invention, which can be either double-stranded or single-stranded, include those nucleic acid molecules that form stable hybrids under stringent hybridization conditions with either a given SEQ ID NO denoted herein and/or with the complement of that SEQ ID NO, which may or may not be denoted herein. Methods to deduce a complementary sequence are known to those skilled in the art.

As used herein, stringent hybridization conditions refer to standard hybridization conditions under which nucleic acid molecules, including oligonucleotides, are used to identify similar nucleic acid molecules. Such standard conditions are disclosed, for example, in Sambrook et al., *Molecular Cloning: A Laboratory Manual*, Cold Spring Harbor Labs Press, 1989. Sambrook et al., ibid., is incorporated by reference herein in its entirety (see specifically, pages 9.31–9.62, 11.7 and 11.45–11.61). Stringent hybridization conditions typically permit isolation of nucleic acid molecules having at least about 70% nucleic acid sequence identity with the nucleic acid molecule being used to probe in the hybridization reaction. Formulae to calculate the appropriate hybridization and wash conditions to achieve hybridization permitting 30% or less mismatch of nucleotides are disclosed, for example, in Meinkoth et al., 1984, *Anal. Biochem.* 138, 267–284; Meinkoth et al., ibid., is incorporated by reference herein in its entirety. Examples of such conditions include, but are not limited to, the following: Typically, hybridization conditions include high ionic strength (6×SSC or 6×SSPE) at a temperature that is 20–25° C. below the $T_m$, as calculated according to the guidelines set forth below. Washing conditions are typically at a salt concentration and temperature that is approximately 12–20° C. below the calculated $T_m$ of the hybrid. For hybridizations between molecules larger than about 100 nucleotides, the $T_m$ (melting temperature) can be estimated by $T_m=81.5° C.+16.6(\log_{10}[Na^+])+0.41$ (fraction G+C)$-0.63$(%formamide)$-(600/l)$, where l is the length of the hybrid in base pairs. Specific parameters that affect this equation are discussed in detail on page 9.51 of Sambrook et al., supra. For hybridizations between smaller nucleic acid molecules, $T_m$ can be calculated by: $T_m=1.5+16.6(\log_{10}[Na^+])+0.41$(fraction G+C)$-(600/N)$, where N=the chain length (Sambrook et al., supra, page 11.46). Alternatively, $T_m$ can be calculated empirically as set forth in Sambrook et al., supra, pages 11.55 to 11.57.

In one embodiment of the present invention, the first nucleic acid sequence encodes a protein comprising an enzymatically active portion of human MnSOD. In another embodiment, the first nucleic acid sequence encodes human MnSOD or a naturally occurring allelic variant thereof. In yet another embodiment, the first nucleic acid sequence comprises SEQ ID NO:1. SEQ ID NO:1 encodes a protein having an amino acid sequence which is represented herein as SEQ ID NO:2.

Accordingly, a first nucleic acid sequence encoding a protein comprising an enzymatically active portion of MnSOD includes naturally occurring allelic variants and MnSOD-encoding nucleic acid sequences modified by nucleotide insertions, deletions, substitutions, and/or inversions (i.e., nucleic acid sequence homologues) in a manner such that the modifications do not substantially interfere with the nucleic acid molecule's ability to encode an enzymatically active portion of an MnSOD protein or to form stable hybrids under stringent conditions with naturally occurring MnSOD proteins. A first nucleic acid sequence encoding a protein comprising an enzymatically active portion of MnSOD can include degeneracies. As used herein, nucleotide degeneracies refers to the phenomenon that one amino acid can be encoded by different nucleotide codons. Thus, the nucleic acid sequence that encodes an enzymatically active portion of an MnSOD protein can vary due to degeneracies.

An allelic variant (i.e., a naturally occurring allelic variant) of an MnSOD nucleic acid molecule is a nucleic acic molecule that occurs at essentially the same locus (or loci) in the genome as the gene encoding the native molecule, but which, due to natural variations caused by, for example, mutation or recombination, has a similar but not identical sequence. Allelic variants typically encode proteins having similar activity to that of the protein encoded by the gene to which they are being compared. One class of allelic variants can encode the same protein but have different nucleic acid sequences due to the degeneracy of the genetic code. Allelic variants can also comprise alterations in the 5' or 3' untranslated regions of the gene (e.g., in regulatory control regions). Allelic variants are well known to those skilled in the art.

An MnSOD-encoding nucleic acid molecule homologue can be produced using a number of methods known to those skilled in the art (see, for example, Sambrook et al., ibid.). For example, nucleic acid molecules can be modified using a variety of techniques including, but not limited to, by classic mutagenesis and recombinant DNA techniques (e.g., site-directed mutagenesis, chemical treatment, restriction enzyme cleavage, ligation of nucleic acid fragments and/or PCR amplification), or synthesis of oligonucleotide mixtures and ligation of mixture groups to "build" a mixture of nucleic acid molecules and combinations thereof. Nucleic acid molecule homologues can be selected by hybridization with a portion of a native MnSOD-encoding nucleic acid sequence or by screening the function of a protein encoded by a nucleic acid molecule (e.g., MnSOD enzymatic activity, as described above).

As used herein, polyanionic polysaccharides or proteoglycans on endothelial cell surfaces comprise "heparin-like" substances, including, but not limited to, heparin (a highly sulfated glycosaminoglycan) and heparan sulfate. Such polyanionic polysaccharides or proteoglycans are well known in the art. According to the present invention, a second nucleic acid sequence encoding a peptide that binds to such heparin-like substances can be any sequence encoding a peptide or protein (the terms peptide and protein can be used interchangeably herein) having the readily identifiable characteristic of binding to heparin, heparan sulfate, or other polyanionic polysaccharides or proteoglycans. Methods for determining such binding ability are well known in the art. One example of such a method is described in detail in Example 3. Preferably, a peptide that binds to polyanionic polysaccharides or proteoglycans according to the present invention can be eluted from such heparin-like substances at a salt concentration (NaCl concentration) greater than about 0.15 M.

Structurally, a second nucleic acid sequence encoding a peptide that binds to polyanionic polysaccharides or proteoglycans on endothelial cell surfaces (also referred to herein as "the binding peptide") has at least the following characteristics. First, such a nucleic acid sequence encodes a peptide having an amino acid sequence with at least 5, and more preferably, at least 6, positively charged amino acid residues within any ten-residue region of the amino acid sequence. Such positively charged amino acid residues can be any combination of arginine and/or lysine residues within a ten-residue region of the amino acid sequence. For example, it is known that a naturally occurring variant of human ECSOD exists, named R213G, which contains the sequence, Arg-Lys-Lys-Gly-Arg-Arg, represented herein as SEQ ID NO:3. This ECSOD binds to heparin, even though a glycine is present among the five positively charged amino acid residues. Therefore, a nucleic acid sequence encoding a peptide having at least five positively charged amino acid residues within any ten-residue region of the amino acid sequence of the protein could, for example, have 2–3 or more positively charged residues, followed by one or a few neutral residues, followed by 2–3 or more positively charged residues, and still be expected to bind to polyanionic polysaccharides or proteoglycans or endothelial cell surfaces (heparin-like substances). As another example, a sequence having four positively charged residues followed by two neutral residues followed by four positively charged residues would be expected to bind tightly to polyanionic polysaccharides or proteoglycans on endothelial cell surfaces.

Second, in order to protect the positively charged amino acid residues from proteolytic cleavage in plasma in vivo, such a nucleic acid sequence encodes a peptide having an amino acid sequence that is capped at the end of the peptide that is not attached to the above-described first nucleic acid sequence by at least one, and preferably at least two, and more preferably at least three amino acid residues that are poorly hydrolyzable by human plasma carboxypeptidases. Such amino acid residues can be any combination of residues having such characteristic including, but not limited to, proline, alanine, and/or leucine. As used herein, the term "capped" refers to a sequence which is located at a terminal end of a peptide or protein which protects the remainder of the peptide or protein, for example, by preventing the degradation of the peptide by human plasma carboxypeptidases. Therefore, this amino acid "cap" on the binding peptide could be located at either the N-terminal or the C-terminal end of the peptide, depending on the position of the binding peptide in the mut-MnSOD protein.

Such a nucleic acid sequence encoding a peptide having the above-identified characteristics can have any number of additional amino acid residues which maintain the ability of the peptide to bind to heparin-like substances as described above. In particular, additional residues can include any number of residues that ensure that the peptide has enough stearic flexibility to allow binding to a surface. For example, glycine is an amino acid residue known to provide such flexibility and could be used in a "linker" sequence to link the binding peptide to the rest of the mutant MnSOD molecule.

In one embodiment, the second nucleic acid sequence encoding a peptide that binds to polyanionic polysaccharides and proteoglycans on endothelial cell surfaces encodes a protein comprising a portion of extracellular superoxide dismutase-C (ECSOD-C) which binds to heparin. In another embodiment, the second nucleic acid sequence encodes a peptide comprising the C-terminal region of ECSOD-C, or an allelic variant thereof, that is sufficient to bind to heparin, and more preferably, the 26 C-terminal amino acid residues of native ECSOD-C or an allelic variant thereof. Allelic variants have been described in detail above. In another embodiment, a second nucleic acid sequence useful in the isolated nucleic acid molecule of the present invention comprises SEQ ID NO:4. SEQ ID NO:4 encodes a 26-residue peptide having an amino acid sequence which is represented herein as SEQ ID NO:5.

In an alternate embodiment, the second nucleic acid sequence encoding a peptide that binds to polyanionic polysaccharides and proteoglycans on endothelial cell surfaces encodes a protein comprising the 22 C-terminal amino acid residues of native ECSOD-C (positions 5–26 of SEQ ID NO:5) or an allelic variant thereof, and further comprises a relatively non-hydrophobic sequence of additional amino acid residues which provide stearic flexibility to allow binding of the peptide encoded by the second nucleic acid sequence to a surface.

An isolated nucleic acid molecule of the present invention, comprising the first and second nucleic acid sequences as described above, can additionally comprise any number of other nucleic acid sequences positioned before, after, and between the first and second nucleic acid sequences on the nucleic acid molecule. For example, additional nucleic acid sequences can be added by designing "linker" sequences which would be positioned between the first and second nucleic acid sequences, for instance, by adding restriction sites to a primer used to clone one or more of the nucleic acid sequences into a single nucleic acid molecule. Methods for adding nucleotides to a cloned sequence are well known in the art. Preferably, such additional nucleic acid sequences do not encode a particular protein, although in some embodiments, such sequences may encode a fusion segment, such that a mutant-MnSOD fusion protein is encoded. Fusion segments are described in detail below.

In one embodiment of the present invention, an isolated nucleic acid molecule of the present invention, comprising said first and second nucleic acid sequences, hybridizes under stringent hybridization conditions (set forth above) to a nucleic acid molecule having a nucleic acid sequence represented by SEQ ID NO:6 or SEQ ID NO:8, or to a nucleic acid molecule comprising both of the nucleic acid sequences represented by SEQ ID NO:1 and SEQ ID NO:4. SEQ ID NOs:1, 4, 6 and 8 are described in detail in Example 1. In yet another embodiment, an isolated nucleic acid molecule of the present invention comprises SEQ ID NO:6, SEQ ID NO:8, or a nucleic acid molecule comprising both SEQ ID NO:1 and SEQ ID NO:4. In a preferred embodiment, an isolated nucleic acid molecule of the present invention hybridizes under stringent hybridization conditions with nucleic acid molecule pGB1MMN. In another embodiment, an isolated nucleic acid molecule of the present invention comprises nucleic acid molecule pGB1MMN. The construction and nucleotide sequence of pGB1MMN is described in detail in Examples 1 and 2.

Preferably, an isolated nucleic acid molecule of the present invention encodes a protein that binds to polyanionic polysaccharides or proteoglycans on endothelial cell surfaces, such as heparin or heparan sulfate. An isolated nucleic acid molecule of the present invention also preferably encodes a protein that protects a mammal from oxidative damage. In one embodiment, a protein encoded by an isolated nucleic acid molecule of the present invention protects a mammal from a condition selected from the group of pulmonary inflammatory injury, lung disease, cancer, hypoxia, ischemia reperfusion injury, hyperoxia, atherosclerosis, arthritis, lupus erythematosus, hypertension, or neutrophil-mediated inflammation. Such proteins are discussed in detail below.

Knowing the nucleic acid sequences of native SOD nucleic acid molecules, such as native ECSOD or native MnSOD nucleic acid molecules allows one skilled in the art to, for example, (a) make copies of those nucleic acid molecules, (b) obtain nucleic acid molecules including at least a portion of such nucleic acid molecules (e.g., nucleic acid molecules including full-length genes, full-length coding regions, regulatory control sequences, truncated coding regions), and (c) obtain SOD nucleic acid molecules from a variety of mammaliar species. Such nucleic acid molecules can be obtained in a variety of ways including screening appropriate expression libraries with antibodies; traditional cloning techniques using oligonucleotide probes to screen appropriate libraries or DNA; and PCR amplification of appropriate libraries or DNA using oligonucleotide primers. Techniques to clone and amplify genes are disclosed, for example, in Sambrook et al., ibid.

The present invention includes a nucleic acid molecule of the present invention operatively linked to one or more transcription control sequences to form a recombinant molecule. The phrase "recombinant molecule" primarily refers to a nucleic acid molecule or nucleic acid sequence operatively linked to a transcription control sequence, but can be used interchangeably with the phrase "nucleic acid molecule" which is administered to a mammal. The phrase "operatively linked" refers to linking a nucleic acid molecule to a transcription control sequence in a manner such that the molecule is able to be expressed when transfected (i.e., transformed, transduced or transfected) into a host cell. Transcription control sequences are sequences which control the initiation, elongation, and termination of transcription. Particularly important transcription control sequences are those which control transcription initiation, such as promoter, enhancer, operator and repressor sequences. Suitable transcription control sequences include any transcription control sequence that can function in at least one of the recombinant cells of the present invention. A variety of such transcription control sequences are known to those skilled in the art. Preferred transcription control sequences include those which function in mammalian, bacteria, insect cells, and preferably in bacterial cells. More preferred transcription control sequences include, but are not limited to, promoters associated with $E.$ $coli$ sodA, simian virus 40 (SV-40), β-actin, retroviral long terminal repeat (LTR), Rous sarcoma virus (RSV), cytomegalovirus (CMV), tac, lac, trp, trc, oxy-pro, omp/lpp, rrnB, bacteriophage lambda ($\lambda$) (such as $\lambda p_L$ and $\lambda p_R$ and fusions that include such promoters), bacteriophage T7, T7lac, bacteriophage T3, bacteriophage SP6, bacteriophage SPo1, metallothionein, alpha mating factor, Pichia alcohol oxidase, alphavirus subgenomic promoters (such as Sindbis virus subgenomic promoters), baculovirus, $Heliothis$ $zea$ insect virus, vaccinia virus and other poxviruses, herpesvirus, and adenovirus transcription control sequences, as well as other sequences capable of controlling gene expression in eukaryotic or prokaryotic cells. Additional suitable transcription control sequences include tissue-specific promoters and enhancers (e.g., T cell-specific enhancers and promoters). Transcription control sequences of the present invention can also include naturally occurring transcription control sequences naturally associated with a gene encoding an MnSOD protein.

Recombinant molecules of the present invention, which can be either DNA or RNA, can also contain additional regulatory sequences, such as translation regulatory sequences, origins of replication, and other regulatory sequences that are compatible with the recombinant cell. In one embodiment, a recombinant molecule of the present invention also contains secretory signals (i.e., signal segment nucleic acid sequences) to enable an expressed mutant-MnSOD protein of the present invention to be secreted from the cell that produces the protein.

One or more recombinant molecules of the present ain-vention can be used to produce an encoded product (i.e., an mutant-MnSOD protein), which can be used in a method of the present invention. In one embodiment, an encoded product is produced by expressing a nucleic acid molecule as described herein under conditions effective to produce the protein. A preferred method to produce an encoded protein is by transfecting a host cell with one or more recombinant molecules to form a recombinant cell. Suitable host cells to transfect include any suitable host cell that can be transfected. Host cells can be either untransfected cells or cells that are already transformed with at least one nucleic acid molecule. Host cells according to the present invention can be any cell capable of producing a mutant-MnSOD accordin to the present invention. A preferred host cell includes a bacterial or yeast host cell, and more preferably, a bacterial host cell, and even more preferably an $Escherichia$ $coli$ host cell.

It may be appreciated by one skilled in the art that use of recombinant DNA technologies can improve expression of transfected nucleic acid molecules by manipulating, for example, the number of copies of the nucleic acid molecules within a host cell, the efficiency with which those nucleic acid molecules are transcribed, the efficiency with which the resultant transcripts are translated, and the efficiency of post-translational modifications. Recombinant techniques useful for increasing the expression of nucleic acid molecules of the present invention include, but are not limited to, operatively linking nucleic acid molecules to high-copy number plasmids, integration of the nucleic acid molecules into one or more host cell chromosomes, addition of vector stability sequences to plasmids, substitutions or modifications of transcription control signals (e.g., promoters, operators, enhancers), substitutions or modifications of translational control signals (e.g., ribosome binding sites, Shine-Dalgarno sequences), modification of nucleic acid molecules of the present invention to correspond to the codon usage of the host cell, and deletion of sequences that destabilize transcripts. The activity of an expressed recombinant protein of the present invention may be improved by fragmenting, modifying, or derivatizing nucleic acid molecules encoding such a protein.

Another embodiment of the present invention includes a recombinant cell comprising a host cell transformed with one or more recombinant molecules of the present invention. Transformation of a nucleic acid molecule into a cell can be accomplished by any method by which a nucleic acid molecule can be inserted into the cell. Transformation techniques include, but are not limited to, transfection, electroporation, microinjection, lipofection, adsorption, and protoplast fusion.

Yet another embodiment of the present invention is an isolated recombinant molecule comprising: (a) a nucleic acid sequence encoding an $E.$ $coli$ sodA promoter and Shine-Dalgarno sequence of $E.$ $coli$ manganese superoxide dismutase (MnSOD); (b) an ATG translation initiation codon; (c) a nucleic acid sequence encoding human MnSOD; (d) a nucleic acid sequence encoding a C-terminal region of human extracellular superoxide dismutase; (e) a nucleic acid sequence encoding a transcription termination signal of $E.$ $coli$ MnSOD; and, (f) a nucleic acid sequence comprising a bacterial origin of replication sequence. Various embodiments of such a recombinant molecule have been described in detail above. A particularly preferred recombinant molecule of the present invention is pGB1MMN.

One embodiment of the present invention is an isolated mutant manganese superoxide dismutase (mutant MnSOD) protein. Such protein comprises an enzymatically active portion of MnSOD and a region which binds to polyanionic polysaccharides or proteoglycans on endothelial cell surfaces. The region of the mutant MnSOD protein that binds to polyanionic polysaccharides or proteoglycans is located at either the C-terminal or the N-terminal end of the mutant-MnSOD protein. It is to be noted that the term "a" or "an" entity refers to one or more of that entity; for example, a protein refers to one or more proteins, or to at least one protein. As such, the terms "a" (or "an"), "one or more" and "at least one" can be used interchangeably herein. It is also to be noted that the terms "comprising", "including", and "having" can be used interchangeably. An isolated mutant-MnSOD protein can be produced using recombinant DNA technology or be synthesized chemically, as will be discussed in detail below.

In one embodiment of the present invention, the isolated mutant MnSOD is encoded by an isolated nucleic acid molecule of the present invention as described in detail above. Such an isolated nucleic acid molecule comprises a first nucleic acid sequence encoding a protein comprising an enzymatically active portion of MnSOD and a second nucleic acid sequence encoding a peptide that has the above described endothelial cell binding ability. Various embodiments of proteins encoded by such first and second nucleic acid sequences have been described in detail above. In one embodiment of the present invention, the mutant MnSOD protein of the present invention is encoded by a nucleic acid molecule that hybridizes under stringent hybridization conditions to a nucleic acid molecule having a nucleic acid sequence represented by SEQ ID NO:6. In another embodiment, the mutant MnSOD protein is encoded by a nucleic acid molecule having a nucleic acid sequence SEQ ID NO:6. In yet another embodiment, the mutant MnSOD protein is encoded by a nucleic acid molecule comprising both nucleic acid sequence SEQ ID NO:1 and SEQ ID NO:4.

In another embodiment mutant MnSOD proteins of the present invention are encoded by a nucleic acid molecule that hybridizes under stringent hybridization conditions to the nucleic acid molecule pGB1MMN. In another embodiment, a mutant MnSOD protein of the present invention is encoded by a nucleic acid molecule pGB1MMN.

In yet another embodiment, the mutant MnSOD protein of the present invention comprises an amino acid sequence selected from the group of an amino acid sequence represented by SEQ ID NO:7, an amino acid sequence comprising both SEQ ID NO:2 and SEQ ID NO:5, or an amino acid sequence that differs from SEQ ID NO:7 or from an amino acid sequence comprising both SEQ ID NO:2 and SEQ ID NO:5 by one or a few amino acid insertions, deletions, or substitutions that do not substantially affect the MnSOD enzymatic activity of the isolated mutant MnSOD protein or the ability of the protein to bind to polyanionic polysaccharides or proteoglycans on endothelial cell surfaces, as compared to the mutant MnSOD protein having the amino acid sequence of SEQ ID NO:7 or the mutant protein having the amino acid sequence comprising both SEQ ID NO:2 and SEQ ID NO:5. In one embodiment, the mut-MnSOD is a hybrid tetrameric protein comprising the mature human MnSOD and the C-terminal 26-amino acid basic peptide from human ECSOD.

One embodiment of the present invention is a fusion protein that includes a mutant MnSOD-containing domain attached to one or more fusion segments. Suitable fusion segments for use with the present invention include, but are not limited to, segments that can: enhance a protein's stability; act to enhance the enzymatic activity of MnSOD; and/or assist purification of a mutant MnSOD protein (e.g., by affinity chromatography). A suitable fusion segment can be domain of any size that has the desired function (e.g., imparts increased stability, imparts increased enzymatic activity to a protein, and/or simplifies purification of a protein). Fusion segments can be joined to amino and/or carboxyl termini of the mutant MnSOD-containing domain of the protein and can be susceptible to cleavage in order to enable straight-forward recovery of a mutant MnSOD protein. Fusion proteins are preferably produced by culturing a recombinant cell transformed with a fusion nucleic acid molecule that encodes a protein including the fusion segment attached to either the carboxyl and/or amino terminal end of a mutant MnSOD-containing domain. Preferred fusion segments include a metal binding domain (e.g., a poly-histidine segment); an immunoglobulin binding domain (e.g., Protein A; Protein G; T cell; B cell; Fc receptor or complement protein antibody-binding domains); a sugar binding domain (e.g., a maltose binding domain); and/or a "tag" domain (e.g., at least a portion of β-galactosidase, a strep tag peptide, other domains that can be purified using compounds that bind to the domain, such as monoclonal antibodies).

Isolated mutant MnSOD proteins of the present invention can be produced by production and recovery of recombinant proteins and by chemical synthesis of the proteins. In one embodiment, an isolated mutant MnSOD protein of the present invention is produced by culturing a cell capable of expressing the protein under conditions effective to produce the protein, and recovering the protein. A preferred cell to culture is a recombinant cell of the present invention comprising a recombinant nucleic acid molecule encoding a mutant MnSOD of the present invention. Effective culture conditions include, but are not limited to, effective media, bioreactor, temperature, pH and oxygen conditions that permit protein production. An effective medium refers to any medium in which a cell is cultured to produce a mutant MnSOD protein of the present invention. Such medium typically comprises an aqueous medium having assimilable carbon, nitrogen and phosphate sources, and appropriate salts, minerals, metals and other nutrients, such as vitamins. Additionally, an effective medium for producing a recombinant mut-MnSOD protein of the present invention includes addition of manganese to the culture medium such as by the addition of 200 $\mu$M $MnSO_4$ to the medium. Moreover, when the promoter is the *E. coli* MnSOD promoter, to achieve maximal mut-MnSOD expression, paraquat is preferably added to the medium at a concentration of at from about 20 to about 40 $\mu$M. As discussed in the Examples section below, the *E. coli* MnSOD promoter can be induced to very high levels by the herbicidal agent paraquat, which induces an oxidative stress (Hassan et al., 1977, *J. Biol. Chem.* 252:7667–7672). Thus, high level expression of foreign genes cloned downstream from this inducible promoter upon paraquat treatment of the bacterial cultures can be obtained by addition of paraquat to the culture medium. Cells of the present invention can be cultured in conventional fermentation bioreactors, shake flasks, test tubes, microtiter dishes, and petri plates. Culturing can be carried out at a temperature, pH and oxygen content appropriate for a recombinant cell. Such culturing conditions are within the expertise of one of ordinary skill in the art. Preferably, a recombinant cell of the present invention comprising a recombinant nucleic acid molecule encoding a mutant MnSOD of the present invention expresses at least about 10% mut-MnSOD as a percentage of total protein expressed by the recombinant cell, and more preferably at least about 25%, and even more preferably, at least about 50%.

Depending on the vector and host system used for production, resultant proteins of the present invention may either remain within the recombinant cell; be secreted into the fermentation medium; be secreted into a space between two cellular membranes, such as the periplasmic space in *E. coli*; or be retained on the outer surface of a cell or viral membrane.

The phrase "recovering the protein" refers to collecting the whole fermentation medium containing the protein and need not imply additional steps of separation or purification. Mutant MnSOD proteins of the present invention can be purified using a variety of standard protein purification techniques, such as, but not limited to, affinity chromatography, ion exchange chromatography, filtration, electrophoresis, hydrophobic interaction chromatography, gel filtration chromatography, reverse phase chromatography, concanavalin A chromatography, chromatofocusing and differential solubilization. Proteins of the present invention are preferably retrieved in "substantially pure" form. As used herein, "substantially pure" refers to a purity that allows for the effective use of the protein as a therapeutic composition or diagnostic. A therapeutic composition for mammals, for example, should exhibit no substantial toxicity and preferably should be capable of stimulating the production of antibodies in a treated mammal.

The present invention also includes isolated (i.e., removed from their natural milieu) antibodies capable of selectively binding to a mutant MnSOD protein of the present invention (i.e., anti-mutant MnSOD antibodies). As used herein, the term "selectively binds to" refers to the ability of antibodies of the present invention to preferentially bind to specified proteins of the present invention. Binding can be measured using a variety of methods standard in the art including enzyme immunoassays (e.g., ELISA), immunoblot assays, etc.; see, for example, Sambrook et al., ibid.

Isolated antibodies of the present invention can include serum containing such antibodies, or antibodies that have been purified to varying degrees. Antibodies of the present invention can be polyclonal or monoclonal, functional equivalents such as antibody fragments and genetically-engineered antibodies, including single chain antibodies or chimeric antibodies that can bind to more than one epitope.

A preferred method to produce antibodies of the present invention includes (a) administering to a mammal an effective amount of a mutant MnSOD protein or peptide of the present invention to produce the antibodies and (b) recovering the antibodies. In another method, antibodies of the present invention are produced recombinantly using techniques as heretofore disclosed to produce mutant MnSOD proteins of the present invention. Antibodies raised against defined proteins can be advantageous because such antibodies are not substantially contaminated with antibodies against other substances that might otherwise cause interference in a diagnostic assay or side effects if used in a therapeutic composition.

Antibodies of the present invention have a variety of potential uses that are within the scope of the present invention. For example, such antibodies can be used as reagents in assays to detect the presence, in a mammal, of mutant MnSOD and/or as tools to screen expression libraries and/or to recover desired proteins of the present invention from a mixture of proteins and other contaminants.

As discussed above, mutant MnSOD proteins of the present invention, when administered to a mammal, protect the mammal from oxidative damage. Accordingly, included in the present invention is a method to protect a mammal from oxidative damage, comprising administering to the mammal an isolated MnSOD protein of the present invention. In particular, administration of a mutant MnSOD protein can be in the form of a therapeutic composition, comprising the mutant MnSOD protein or a nucleic acid molecule encoding the mutant MnSOD protein, and a pharmaceutically acceptable delivery vehicle.

Oxidative damage refers to cellular damage that occurs as a result of the accumulation of oxygen-free radicals and other oxidative species in cells. Such oxygen-free radicals and oxidative species (e.g. hydrogen peroxide) result from reactive oxygen intermediates produced during various types of stress, caused by conditions such as lung disease, ischemia, hypoxia, exposure to ozone, hyperoxia, inflammatory responses, chemical reactions, ultraviolet or X-ray irradiation, or viral infection.

As discussed above, one embodiment of the present invention is a therapeutic composition to protect a mammal from oxidative damage, comprising: (a) a protective compound selected from the group of: (i) an isolated mutant manganese superoxide dismutase (MnSOD) protein comprising an enzymatically active portion of MnSOD and a C-terminal region which binds to polyanionic polysaccharides or proteoglycans on endothelial cell surfaces; and/or, (ii) an isolated nucleic acid molecule comprising: a first nucleic acid sequence encoding a protein comprising an enzymatically active portion of MnSOD; and, a second nucleic acid sequence encoding a peptide that binds to polyanionic polysaccharides or proteoglycans on endothelial cell surfaces; and, (b) a pharmaceutically acceptable delivery vehicle.

Administration of a mutant-MnSOD protein or therapeutic composition of the present invention to treat oxidative damage in a mammal is particularly useful when such mammal has a condition selected from the group of pulmonary inflammatory injury, lung disease, cancer, hypoxia, ischemia reperfusion injury, hyperoxia, atherosclerosis, arthritis, lupus erythematosus, hypertension, or neutrophil-mediated inflammation. "A condition", as used herein, refers to a disease, or any deviation from normal health of a mammal and includes disease symptoms as well as conditions in which a deviation (e.g., infection, environmental trigger, gene mutation, genetic defect, etc.) has occurred but symptoms are not yet manifested. Having a condition, therefore, can include being predisposed to such a condition or disease (e.g. due to genetic predisposition or predisposition due to environmental factors or other medical conditions or procedures).

Hypoxia is a condition characterized by abnormally low levels of oxygen in the blood and tissues. Ischemia-reperfusion injury is a type of injury that is due to damage to a tissue resulting from oxygenation deficiency caused by restriction of blood supply to the tissue. Ischemia reperfusion injury often occurs after organ transplantation. Examples of lung diseases for which a method of the present invention can be particularly useful to treat include, but are not limited to, infant respiratory distress syndrome, adult respiratory distress syndrome, interstitial lung disease, and asthma. The method of the present invention is also useful to treat various inflammatory diseases including, but not limited to, rheumatoid arthritis, inflammatory bowel disease, and several inflammatory skin diseases.

Accordingly, the composition and method of the present invention preferably protect a mammal from oxidative damage such that the mammal is protected from a disease or condition associated with oxidative damage. As used herein, the phrase "to protect a mammal from oxidative damage" refers to reducing the level of oxidative damage in a mammal wherein such damage has already occurred, is occurring, will occur in the future, or may occur in the future. Similarly, the phrase "protected from a disease or condition" refers to reducing the symptoms of the disease; reducing the occurrence of the disease, and/or reducing the severity of the disease. Protecting a mammal can refer to the ability of a therapeutic composition of the present invention, when administered to a mammal, to prevent a disease from occurring and/or to cure or to alleviate disease symptoms, signs or causes. As such, to protect a mammal from a disease includes both preventing disease or condition occurrence (prophylactic treatment) and treating a mammal that has a disease or condition (therapeutic treatment). When used to prevent oxidative damage, such treatment can therefore be administered prior to the potential for such damage to occur. Protecting a mammal from a disease is accomplished by preventing, reducing or eliminating oxidative damage in cells and/or tissues of the mammal. Preferably, oxidative damage, or the potential for oxidative damage, is reduced, optimally, to an extent that the mammal no longer suffers discomfort and/or altered function from oxidative damage. The term, "disease" refers to any deviation from the normal health of a mammal and includes a state when disease symptoms are present, as well as conditions in which a deviation (e.g., infection, gene mutation, genetic defect, etc.) has occurred, but symptoms are not yet manifested.

In preferred embodiments of the method of the present invention, administration of mutant MnSOD and mutant MnSOD therapeutic compositions to a mammal results in binding of the mutant MnSOD to endothelial cell surfaces of the mammal and protects the mammal from oxidative damage. In further embodiments, administration of mutant MnSOD to a mammal protects the mammal from acute lung injury due to oxidative damage. Administration of mutant MnSOD to a mammal can also reduce neutrophil-mediated inflammation in the mammal and/or protect the organs of a donor mammal from pre-transplantation and/or post-transplantation oxidative damage. Methods of assessing these various types of oxidative damage are known in the art, and examples are set forth in the Examples section. In the method wherein organs of a donor mammal are protected from pre-transplanation and/or post-transplantation oxidative damage, mutant MnSOD can be administered to the donor organs or alternatively, to the recipient mammal.

In the method of the present invention, mutant MnSOD proteins and therapeutic compositions comprising mutant MnSOD can be administered to any member of the Vertebrate class, Mammalia, including, without limitation, primates, rodents, livestock and domestic pets. Livestock include mammals to be consumed or that produce useful products (e.g., sheep for wool production). Preferred mammals to protect include humans, dogs, cats, mice, rats, rabbits, sheep, cattle, horses and pigs, with humans being most preferred.

Suitable modes of administration can include, but are not limited to, oral, nasal, intratracheal injection, inhaled, transdermal, rectal, and parenteral routes. Preferred parenteral routes can include, but are not limited to, subcutaneous, intradermal, intravenous, intramuscular and intraperitoneal routes. Administration by inhalation can be by inhaling an aerosol, and intratracheal administration can be by injection directly into the trachea, either directly or via lipid-encapsulation or surfactant. In a preferred embodiment of the present invention, a composition containing a mutant-MnSOD protein of the present invention is administered by a parenteral route.

Preferably, a mutant MnSOD protein of the present invention is administered in a pharmaceutically acceptable delivery vehicle, thus providing a therapeutic composition. In a more preferred embodiment, such a delivery vehicle is capable of slowly releasing the mutant MnSOD protein or the therapeutic composition of the present invention into a mammal. Pharmaceutically acceptable delivery vehicles include, but are not limited to, liposomes, recombinant cells, biocompatible polymers, other polymeric matrices, capsules, microcapsules, microparticles, bolus preparations, osmotic pumps, diffusion devices, lipospheres, transdermal delivery systems, and surfactants. Other delivery vehicles of the present invention include liquids that, upon administration to a mammal, form a solid or a gel in situ. Particularly preferred delivery vehicles of the present invention include lipid capsules or surfactants. Preferred delivery vehicles are also biodegradable (i.e., bioerodible).

When a nucleic acid molecule of the present invention is to be administered to a mammal, preferred delivery vehicles are capable of maintaining a nucleic acid molecule of the present invention in a form that, upon arrival of the nucleic acid molecule to a cell, the nucleic acid molecule is capable of entering the cell and being expressed by the cell. Such delivery vehicles can include metal particles (e.g., gold particles) for use with, for example, a biolistic gun through the skin, artificial lipid-containing delivery vehicles (liposomes and micelles), natural lipid-containing delivery vehicles (cells and cellular membranes), and recombinant virus particle vaccines.

A preferred delivery vehicle of the present invention is capable of maintaining a mutant MnSOD protein of the present invention in the blood of a mammal or preferably at the site undergoing oxidative damage such that the half-life of the protein in the mammal is sufficient to protect the mammal from the oxidative damage. A mutant MnSOD protein of the present invention that is administered in the context of a pharmaceutically acceptable delivery vehicle of the present invention preferably has a half-life in a mammal that is greater than about 5 minutes in a mammal, and more preferably greater than about 4 hours in a mammal, even more preferably greater than about 10 hours in a mammal, and even more preferably, greater than about 20 hours in a mammal.

According to the present invention, an effective administration protocol (i.e., administering a therapeutic composition in an effective manner) comprises suitable dose parameters and modes of administration that result in protection of a mammal from oxidative damage. Effective dose parameters can be determined using methods standard in the art for a particular disease. Such methods include, for example, determination of survival rates, side effects (i.e., toxicity) and progression or regression of disease.

In accordance with the present invention, a suitable single dose size is a dose that is capable protecting a mammal from oxidative damage when administered one or more times over a suitable time period. Doses can vary depending upon the disease being treated. Preferably, a mutant MnSOD protein of the present invention is administered in an amount that is between about 50 U/kg and about 15,000 U/kg body weight of the mammal. It will be obvious to one of skill in the art that the number of doses administered to a mammal is dependent upon the extent of the disease and the response of an individual patient to the treatment. Thus, it is within the scope of the present invention that a suitable number of doses includes any number required to cause regression or prevention of a condition.

The following examples are provided for the purposes of illustration and are not intended to limit the scope of the present invention.

EXAMPLES

In Examples 1–7, the following general materials and methods were employed.

All enzymes used for manipulation of DNA were from New England Biolabs or Stratagene, Inc. Sequencing materials were obtained from United States Biochemicals. All other chemicals were from Sigma Pharmaceuticals. Purified human recombinant Cu,ZnSOD and MnSOD were generously provided by Biotechnology General, Inc. SOD was assayed by the method of McCord and Fridovich (1969, *J. Biol. Chem.* 244:6049–6055).

Data are presented as the mean ±standard error in FIGS. 1–13. Tests for significance were made using a one-way analysis of variance and the differences between specific groups were determined by the Newman-Keuls test.

Isolation of plasmid DNA, preparation of DNA fragments, and DNA ligations were carried out as described by Sambrook et al., supra. Plasmid transformation was performed as described (Hanahan, D., 1983, *J. Mol. Biol.* 166:557–580; this publication is incorporated herein by reference in its entirety). Screening of putative recombinant colonies was done using polymerase chain reaction (PCR) unless specified otherwise. Restriction enzyme digestions and DNA sequencing were performed according to manufacturer's specifications. PCR was performed according to manufacturer's specifications (Perkin Elmer/Cetus).

Example 1

The following example describes the design and construction of a mutant MnSOD nucleic acid molecule of the present invention.

The present inventors constructed a fusion gene encoding a mutant manganese superoxide dismutase (mut-MnSOD) according to the present invention, which mimics the some of the properties of naturally occurring ECSOD. This construct consists of the mature human MnSOD and the carboxylterminal 26-amino acid basic "tail" from ECSOD. This "tail" is responsible for the enzyme's affinity to bind to heparin-like proteoglycans on cell surfaces. The fusion gene was highly expressed in *Escherichia coli* by a novel vector constructed by the present inventors, and the resulting mut-MnSOD was purified.

Figure 1:
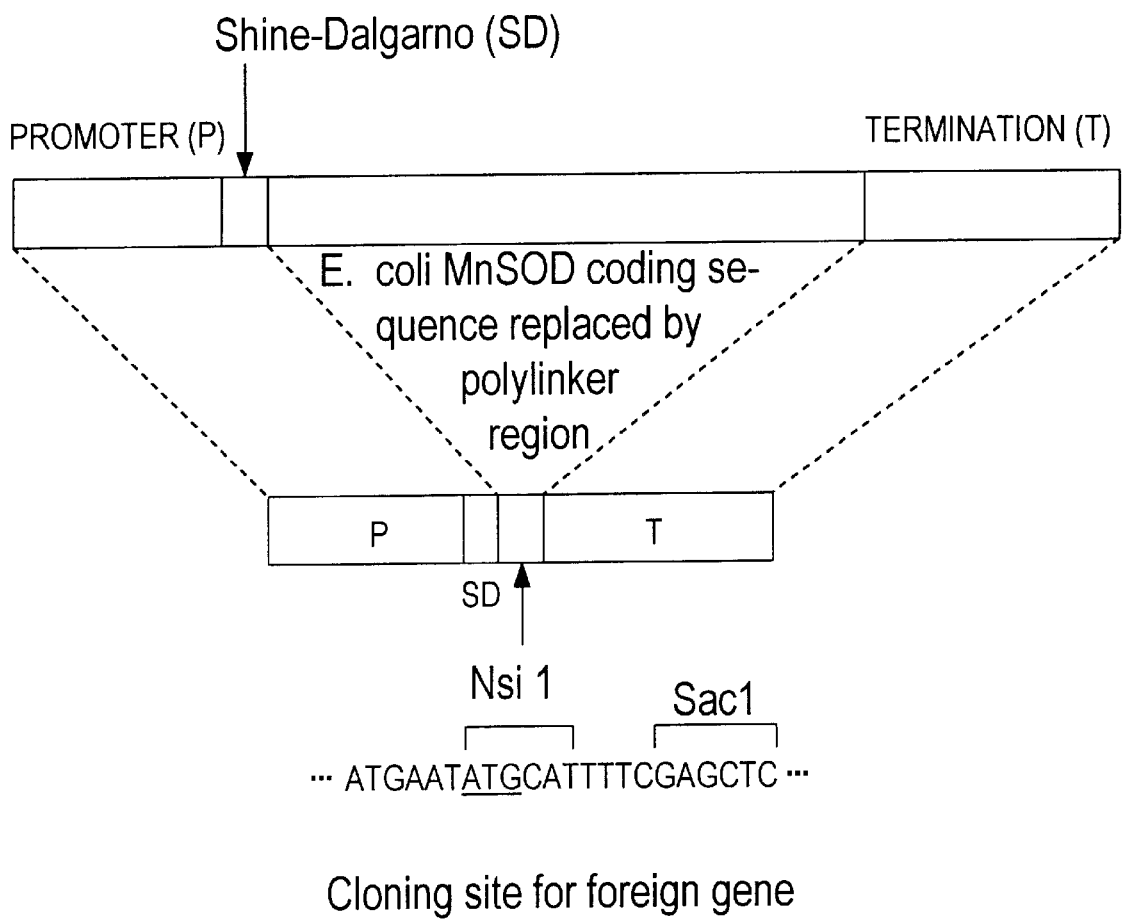
FIG. 1 is a schematic illustration of the strategy for the construction of the expression vector, pGB1.

The strategy for the construction of the expression vector, pGB1, is illustrated in FIG. 1 (SD, Shine-Dalgarno sequence). In general, the coding sequence for bacterial MnSOD was replaced by a synthetic polylinker region which contains unique NsiI and Sacd cloning sites. Both promoter and transcriptional termination signals from the bacterial gene were retained. The ATG initiator codon contained in the NsiI site was the original translation start codon of the *E. coli* MnSOD. The resultant fragment was then cloned into the EcoRI-PstI sites of pUC19, forming a new vector designated pGB1.

Figure 2:
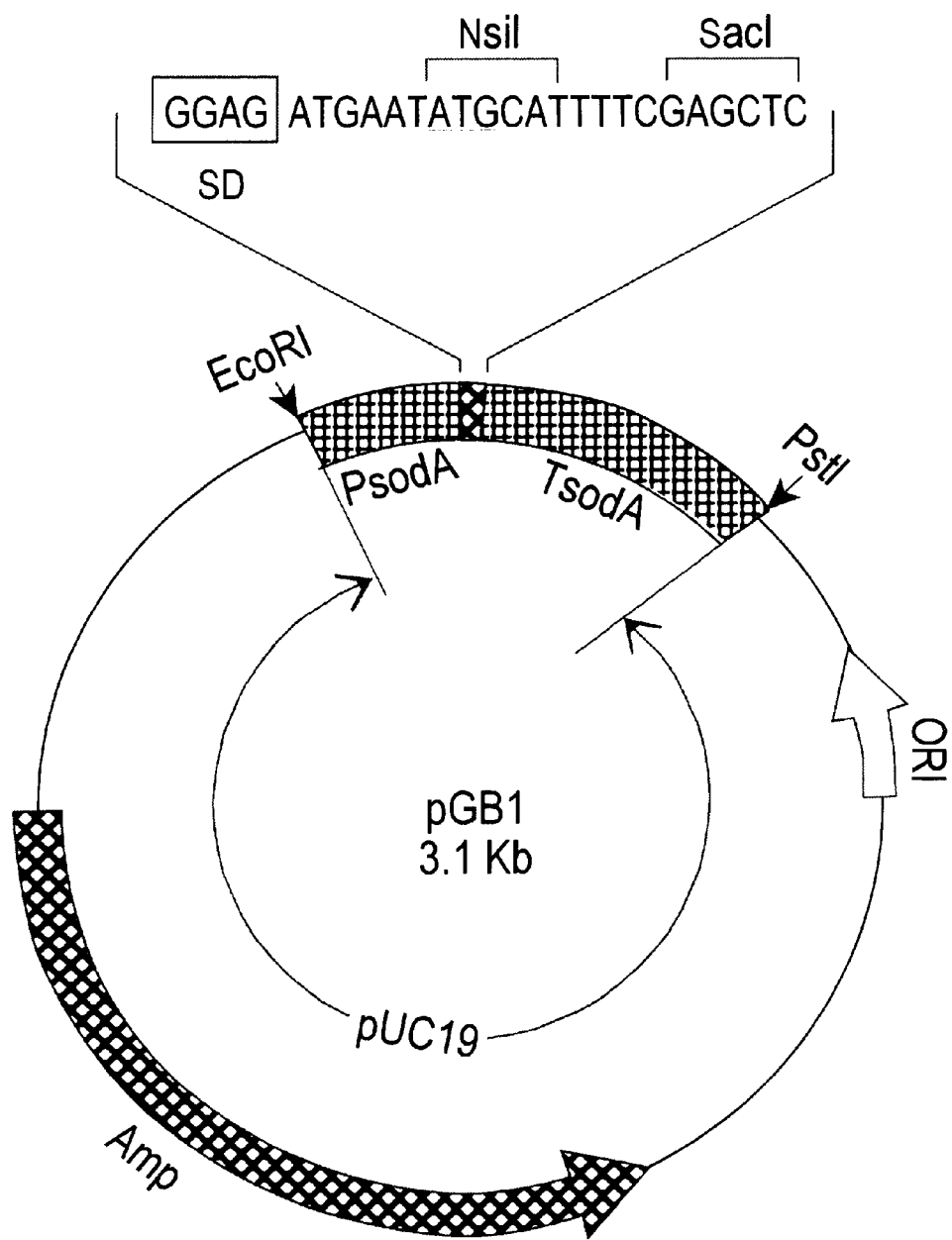
FIG. 2 is a schematic illustration of the structure of pGB1.
Figure 3:
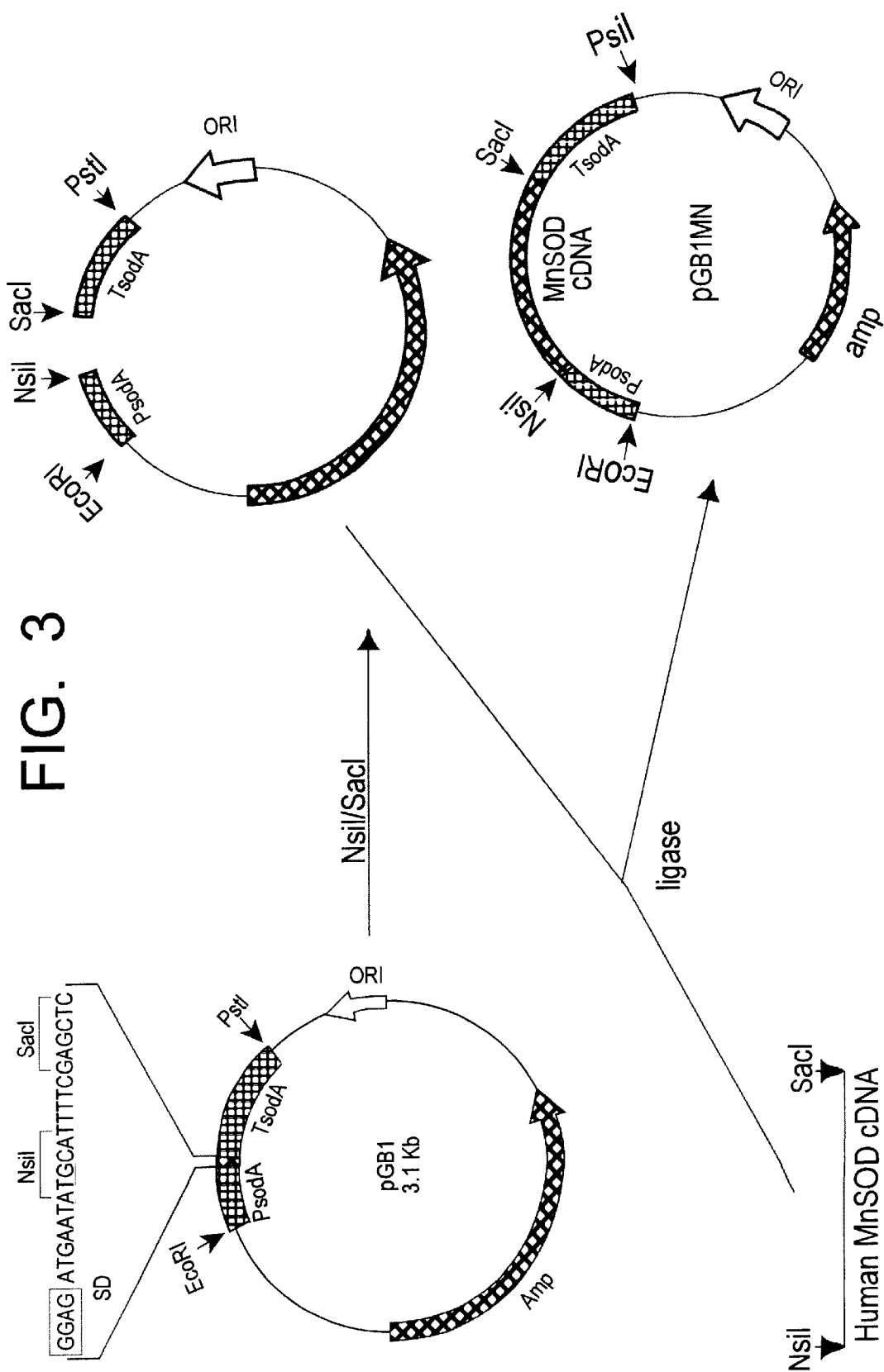
FIG. 3 is a schematic illustration of the construction of a plasmid containing wild-type human MnSOD cDNA, pGB1MN

To create the pGB1 construct, a plasmid (provided by Dr. Paul Gardner) consisting of the *Escherichia coli* MnSOD gene and its associated regulatory elements cloned in pUC9 (Takeda et al., 1986, *Nucleic Acids Res.* 14:4577–4589; incorporated herein by reference in its entirety) was digested with EcoRI and PstI to release two restriction enzyme fragments of 434 bp and 645 bp. The 434 bp fragment was digested with BsrI and a 140 bp fragment containing the promoter (P) and Shine-Dalgarno (SD) sequences was recovered. The 645 bp fragment was digested with BbvI and a 310-bp fragment containing the transcriptional termination signal (T) was recovered. Annealing of two complementary synthetic oligonucleotides of sequence 5'GATGAATATG-CATTTCGAGCTC3' (SEQ ID NO:9) and 5'AATG-GAGCTCGAAATGCATATTCATCTC3' (SEQ ID NO:10) created a double-stranded linker containing internal restriction sites for NsiI and Saci, with terminal 5'BsrI and 3'BbvI cohesive ends. A ligation mixture containing the synthetic linker, the 140 bp and 310 bp fragments as well as a 2.64 kb EcoRI-PstI fragment from pUC19 were incubated overnight with T4 DNA ligase (Bethesda Research Laboratories, Bethesda, M.D.) according to manufacturer's specifications. The resultant plasmid was designated as pGB1 (FIG. 2). PsodA and TsodA indicate the promoter and termination signals from the *E. coli* sodA gene, respectively. The positions of the ampicillin-resistance-encoding gene (Amp) and the bacterial origin of replication (ORI) and the transcriptional polarity are also indicated. The ATG initiator codon contained in the NsiI site was the original translation start codon of the *E.coli* MnSOD. The sequence was confirmed by restriction mapping.

A cDNA encoding human MnSOD was obtained from a human placental cDNA library by the PCR amplification method and was cloned into pBlueScript KS+ (Stratagene). The sequence of the primers used for the PCR reaction are as follows: 5'GGAATTCATGCATAAGCACAGCCTC-CCCGAC3' (represented herein as SEQ ID NO:11) and 5'CGAGCTCTTACCCGGGCTTTTTGCAAGCCATGTA3' (represented herein as SEQ ID NO:12). The 5'(sense)-primer contains an EcoRI upstream of an NsiI restriction endonuclease site. The 3'(antisense)-primer contains a SacI site immediately upstream from the translational stop codon. An XmaI site positioned adjacent to the stop codon allowed ligation of a nucleic acid sequence encoding the ECSOD tail. After corroborating the cloned MnSOD cDNA sequence, the coding region was released by NsiI and SacI restriction enzyme digestion. This fragment, containing the 594 bp nucleic acid sequence represented herein as SEQ ID NO:1, was then subcloned into pGB1 previously digested with the same enzymes. The resultant plasmid was designated as pGB1MN (FIG. 3; shadowed boxes show the relative positions of coding sequences and regulatory elements, PsodA and TsodA, as in FIG. 2). SEQ ID NO:1 encodes a 198-amino acid residue protein having a amino acid sequence represented herein as SEQ ID NO:2.

Figure 4:
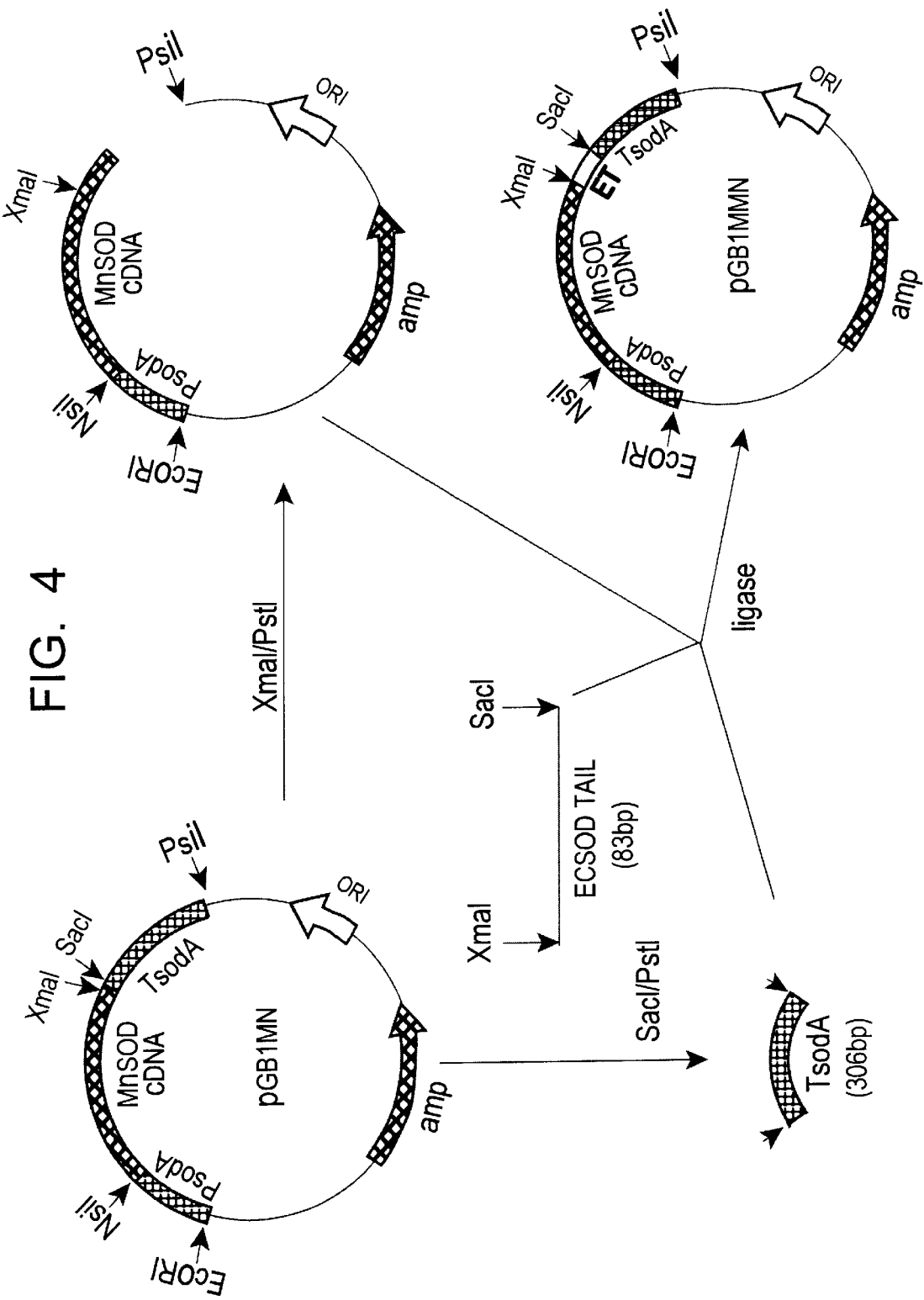
FIG. 4 is a schematic illustration of the construction of a plasmid encoding mut-MnSOD, pGB1MMN.

The pGB1MN plasmid was then used for the high-level expression of human MnSOD and for the subsequent construction of the mut-MnSOD gene. It should be noted that the cloning strategy introduces two additional residues, a methionine (to provide an initial methionine start site) and a histidine, at the N-terminus of the nucleic acid sequence SEQ ID NO:1, and two additional residues, proline and glycine, at the C-terminus of the human MnSOD protein (SEQ ID NO:1). To create a mut-MnSOD gene, an 83 bp cDNA fragment encoding the ECSOD-C "tail" was isolated after XmaI and Sacd double digestion of an ECSOD cDNA-containing recombinant plasmid (obtained from Dr. Ye-Shih Ho). The plasmid pGB1MN was digested with XmaI and PstI and the largest XmaI/PstI fragment was recovered. The plasmid pGB1MN was also digested with SacI/PstI and the small fragment was recovered. These two recovered fragments plus the XmaI/SacI tail fragment from ECSOD were joined in a three-fragment ligation. The new plasmid was designated as pGB1MMN. FIG. 4 shows the construction scheme for this plasmid (ET=DNA fragment encoding human ECSOD C-terminal 26 amino acid basic peptide. The remaining symbols are the same as in FIG. 3). The ECSOD-C C-terminal portion of the pGB1MMN plasmid is a 78 bp fragment represented herein as SEQ ID NO:4. SEQ ID NO:4 encodes a 26-amino acid peptide, the amino acid sequence of which is represented herein as SEQ ID NO:5.

The entire coding nucleic acid sequence of the mutant-MnSOD protein of plasmid pGB1MMN is represented herein by SEQ ID NO:6. SEQ ID NO:6 comprises the nucleic acid sequence for the above-described added methionine and histidine residues, the 594 bp MnSOD-encoding fragment (SEQ ID NO:1), the 78 bp ECSOD tail-encoding fragment (SEQ ID NO:4), which includes the nucleic acid sequence encoding the above-described additional proline and glycine residues, and the stop codon. SEQ ID NO:6 encodes a 226 amino acid protein having an amino acid sequence represented herein as SEQ ID NO:7.

The entire pGB1MMN nucleic acid sequence is represented herein as SEQ ID NO:8. SEQ ID NO:6 is located within SEQ ID NO:8 at nucleotide positions 544–1221 of SEQ ID NO:8.

Example 2

The following experiment demonstrates the strength of the promoter used in the pGB1MN plasmid of Example 1.

The *E. coli* MnSOD gene, under the control of its own promoter, can be induced to very high levels by the herbicidal agent paraquat (methyl viologen), which induces an oxidative stress (Hassan et al., 1977, supra). Paraquat short-circuits a portion of the respiratory electron flow, transferring electrons to $O_2$ to make superoxide, creating a condition of oxidative stress. Thus, high level expression of foreign genes cloned downstream from this inducible promoter upon paraquat treatment of the bacterial cultures was expected. In addition, the pUC vector (Vieira et al., 1982, *Gene* 19:259–259; 1982) used as the parent plasmid contains the pBR322 origin of replication which allows high copy number accumulation of the plasmid per cell. As a convenience in cloning foreign genes, a synthetic oligonucleotide linker containing a restriction endonuclease recognition site with an ATG translational start codon was positioned at precisely the optimal distance from the Shine Dalgarno (SD) sequence. In bacterial expression systems, the distance between the SD sequence and the start codon has been shown to be a critical factor for maximal translational efficiency. The merger of favorable characteristics consistently resulted in yields of recombinant protein of at least 30% of the total soluble protein.

The first bacterium chosen as host, *E. coli* sodAsodB, has disrupted genes for the Fe- and MnSODs (Carlioz et al., 1986, *EMBO J.* 5:623–630). Presumably, only the minor periplasmic SOD remains. Thus, nearly all of the observed activity seer in the transformants is contributed by the recombinant plasmid. To test the strength of the promoter, *E. coli* sodAsodB transformed with plasmid pGB1MN (containing the wild type mature portion (i.e., minus signal peptide) of the human MnSOD sequence, plus additional N-terminal methionine and histidine residues and additional proline and glycine C-terminal residues, as described in Example 1) was grown for 12 hours in the presence of increasing concentrations of paraquat and assayed for SOD activity.

Figure 5:
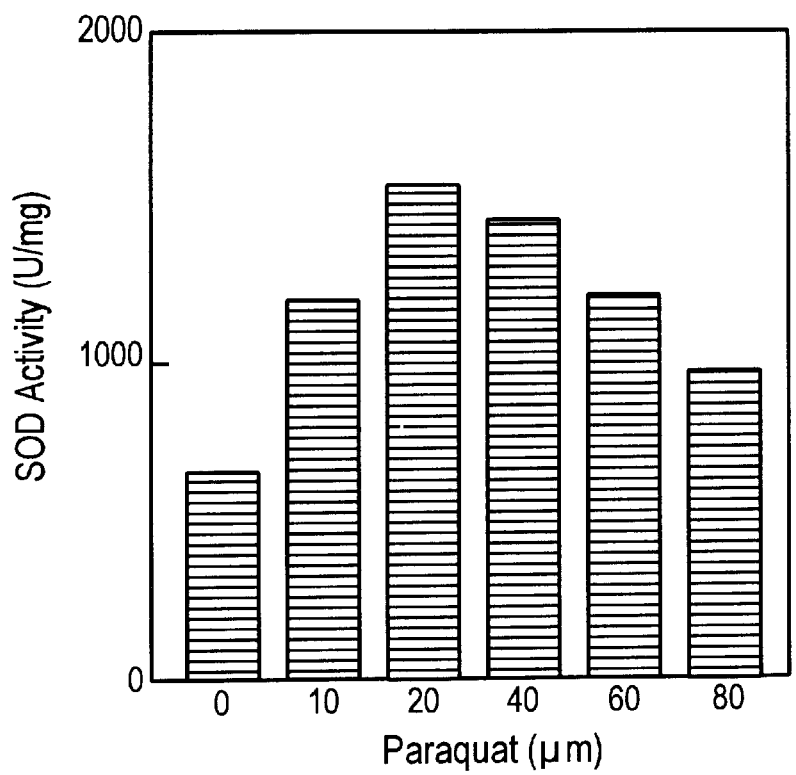
FIG. 5 is a bar graph showing the effects of paraquat treatment on wild-type human MnSOD expression in E. coli.

The results are shown in FIG. 5. Activity of the cell lysates is expressed as U/mg total soluble protein. With no paraquat, the specific activity of the expressed SOD was 658 U/mg. Growth in the presence of oxygen resulted in activation of the promoter, which responded by increasing transcription of the cloned gene, even in the absence of paraquat. Thus, expression under these conditions resulted in a recombinant protein that represented about 25% of total soluble protein (as determined by the Lowry method; Lowry et al., 1951, *J. Biol. Chem.* 193:265–275, which is incorporated herein by reference in its entirety). Growth in 20 μM paraquat further increased SOD activity to 1570 U/mg soluble protein, a value about half that of the pure human enzyme (McCord et al., 1977, In: Michelson, A. M., McCord, J. M., Fridovich, I., eds., *Superoxide and Superoxide Dismutase*, London:Academic Press, pp. 129–138). At the optimal paraquat concentration of 20–40 μM, cell density was similar in paraquat-treated and untreated cells (data not shown). At doses higher than 40 μM, cell density and recovered activity decreased, suggesting an increased toxicity of the inducer. Further expression was undoubtedly limited by the fact that at the optimal concentration of paraquat, the recombinant protein accounted for 50% of the total soluble protein. When these experiments were repeated in the presence of glucose, expression was decreased about 75%. Under anaerobic conditions, expression was nearly completely suppressed to as little as 1 U/mg protein. In addition, the level of expression appeared to vary depending on the age of the colony picked for amplification (data not shown), suggesting that the bacteria lose the plasmid as the colony expands or as the antibiotic becomes less effective. Thus, the optimal conditions for maximum expression of a cloned gene should include aerobic growth in an ampicillin-rich, glucose-free medium, and in the presence of paraquat at a concentration empirically determined.

Example 3

The following example describes the expression and characterization of the biochemical properties of a mutant MnSOD protein of the present invention.

Expression and Purification of Mutant-MnSOD

Because of the hydrophilic nature and basic amino acid content of the C-terminal region added to the mut-MnSOD, plasmid pGB1MMN, described in Example 1, was put into a protease-deficient host, *E. coli* UT5600, to decrease the likelihood of proteolytic degradation of the mutant enzyme after its expression in the host and during its purification. After transformation of competent *E. coli* UT5600 cells, positive clones were identified and cultured at 37° C. for 12 hours in LB medium supplemented with 200 μM $MnSO_4$ and 40 μM paraquat. After centrifugation, the harvested cells were lysed by sonication in a 0.1 M sodium carbonate, 0.6 M NaCl, pH 10.5 buffer. The cell debris was removed from the cell lysate by centrifugation for 30 min. at 10,000×g. The supernatant was collected and subjected to heat treatment at 65° C. for 10 min. The sample was cooled immediately in an ice bath and centrifuged for 10 min. at 10,000×g to remove precipitated protein. Ultrafiltration with Diaflo PM-30 membrane was used to concentrate the supernatant. The sample was then chromatographed through a 15×700 mm column of Sephacryl S-200. Fractions were collected and assayed for SOD activity as described (McCord et al., 1969, *J.Biol.Chem.* 244:6049–6055; and Crapo et al., 1978, *Methods Enzymol.* 53:382–393; both publications of which are incorporated herein by reference in their entirety). Higher molecular weight fractions exhibiting SOD activity were pooled, concentrated by ultrafiltration, and diluted with 10 mM Tris-HCl, pH 7.4, 0.15 M NaCl buffer. This sample was then applied to a heparin-agarose column. Fractions from the heparin-agarose column were eluted using a 0.15 M to 1 M NaCl gradient in the buffer described above and subsequently assayed for SOD activity. Pooled fractions were then subjected to ultrafiltration, changing the buffer during this process to 10 mM potassium phosphate, 0.15 M NaCl, pH 7.4. The specific activity of the purified product was 3,200 standard units/mg protein. The results of the purification process are given in Table 1, reflecting an approximately five-fold purification from crude supernate to final product.

TABLE 1

Results of the purification procedure of the mut-MnSOD expressed in *E. coli* UT5600 transformed with pGB1MMN.

| Purification Step | Total SOD activity (U) | Total protein (mg) | Specific activity (U/mg) | Yield |
|---|---|---|---|---|
| Cell lysate | 427,700 | 881 | 485 | 100% |
| Supernate | 404,800 | 600 | 675 | 95% |
| After heat step | 345,700 | 328 | 1,054 | 81% |
| After gel filtration | 284,500 | 173 | 1,647 | 67% |
| After heparin affinity chromatography | 202,500 | 63 | 3,214 | 47% |

SDS/PAGE Electrophoresis and Chromatography

Purified SOD preparations (purified recombinant native human MnSOD; purified mut-MnSOD; and cellular lysates of recombinants expressing mutant MnSOD) were submitted to SDS/PAGE gel (data not shown). The results confirmed that the expressed mut-MnSOD represents a substantial fraction (about 20%) of the total soluble protein. The MnSOD without the "tail" (i.e., native human MnSOD expression product of plasmid pGB1MN) was expressed to slightly higher levels. Purified mut-MnSOD (95% purity) showed a single protein band with an apparent subunit molecular weight of 25 to 26 kDa, in agreement with the predicted molecular weight of 25,637. The subunit molecular weight of the expressed MnSOD without the "tail" was about 22.5 kDa.

Figure 6:
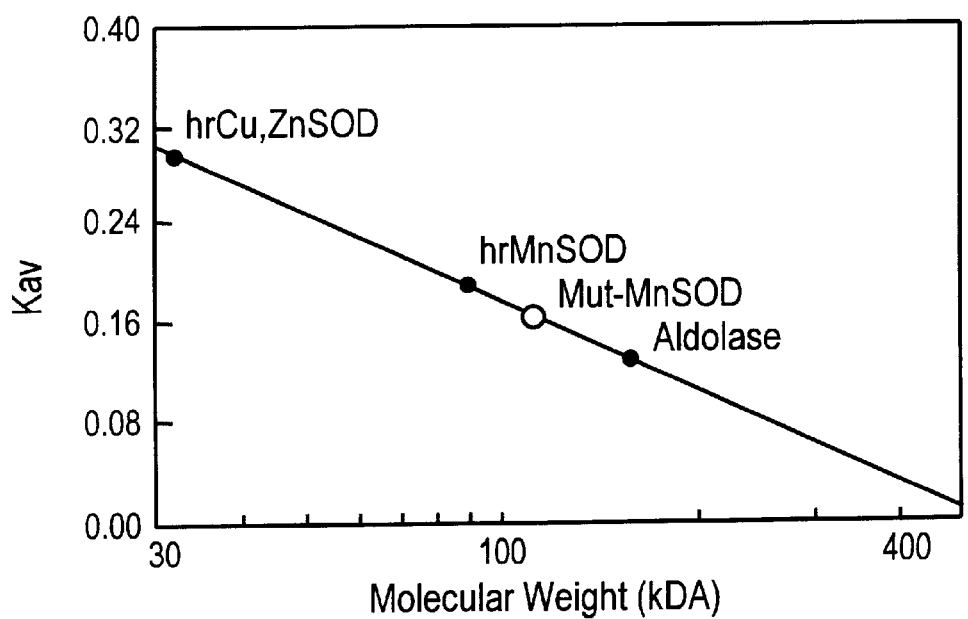
FIG. 6 is a graph illustrating the results of gel filtration chromatography of mut-MnSOD, compared to other SODs.

For native molecular size estimation, a 0.5 ml sample of the purified mutant-MnSOD protein described above was applied to a Sephacryl S-200 column as described above but in 10 mM potassium phosphate, pH 7.4, 0.15 M NaCl. The column had been previously calibrated with the proteins aldolase (158 kDa), native human MnSOD (89.9 kDa) and native human Cu,ZnSOD (31.6 kDa). Absorbance at 280 nm was monitored and Kav (partition coefficient) of each sample was calculated according to the following equation: $K_{av}=V_e-V_oV_t/V_o$, where $V_e$ is the elution volume, $V_o$ is the void volume, and $V_t$ is the total volume of the gel bed. The apparent molecular weight, as determined by FIG. 6, is about 104 kDa, in good agreement with the predicted molecular weight of 102,548 for the tetrameric protein.

No differences were found in specific activity between the mut-MnSOD and the native MnSOD. The similarity of specific activity between the native (3100 Units/ml) and mutant enzyme (3200 Units/ml) suggests that the C-terminal heparin sticky "tail" does not affect the catalytic function of the mutant enzyme.

Heparin Affinity Chromatography

Figure 7:
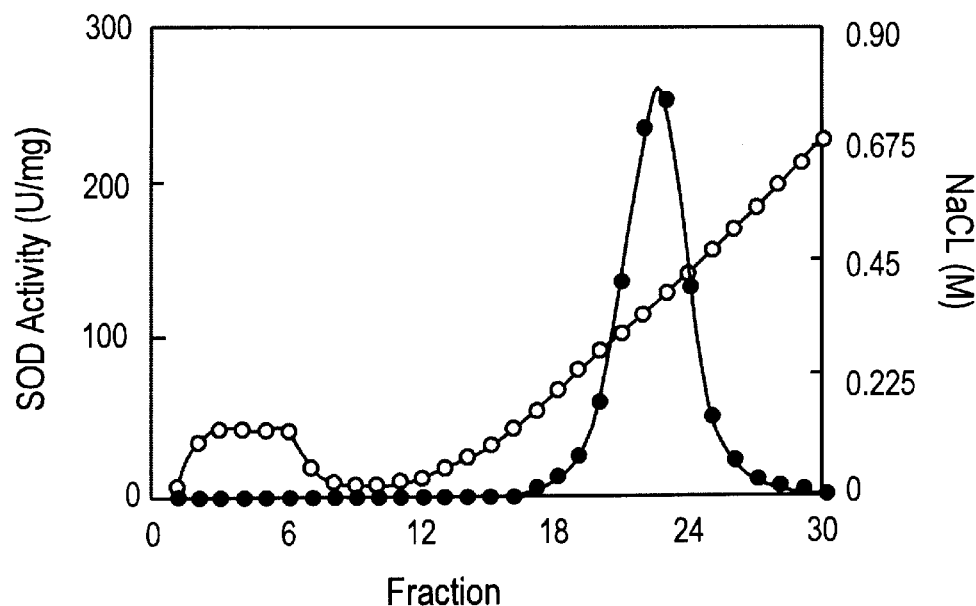
FIG. 7 is a line graph showing the binding and elution of mut-MnSOD to a heparin affinity column.

An aliquot of the purified mutant-MnSOD preparation described above (about 750 units) was applied to a small (1 ml bed volume) column of heparin-agarose (Sigma) in 10 mM Tris-HCl buffer, pH 7.4. The column was washed with this buffer to remove unbound enzyme, and then eluted with a gradient of 0 to 2.0 M NaCl. Fractions were assayed for SOD activity and for conductivity. FIG. 7 shows that the mut-MnSOD (●) eluted from the column as a single symmetrical peak at 0.35 M NaCl (SOD activity expressed as units/ml of fraction volume; NaCl concentration was determined by conductivity (○) of each fraction). Under the same conditions, native MnSOD did not bind to the column (data not shown). Because the physiological salt concentration is approximately 0.15 M, it was predicted that mut-MnSOD would bind to the glycosoaminoglycans of endothelial cell surfaces under the same conditions. This prediction was corroborated by the results obtained in the isolated perfused heart model (See FIG. 8), wherein a bolus dose of heparin displaced the mut-MnSOD which had previously bound to the heart.

Figure 8:
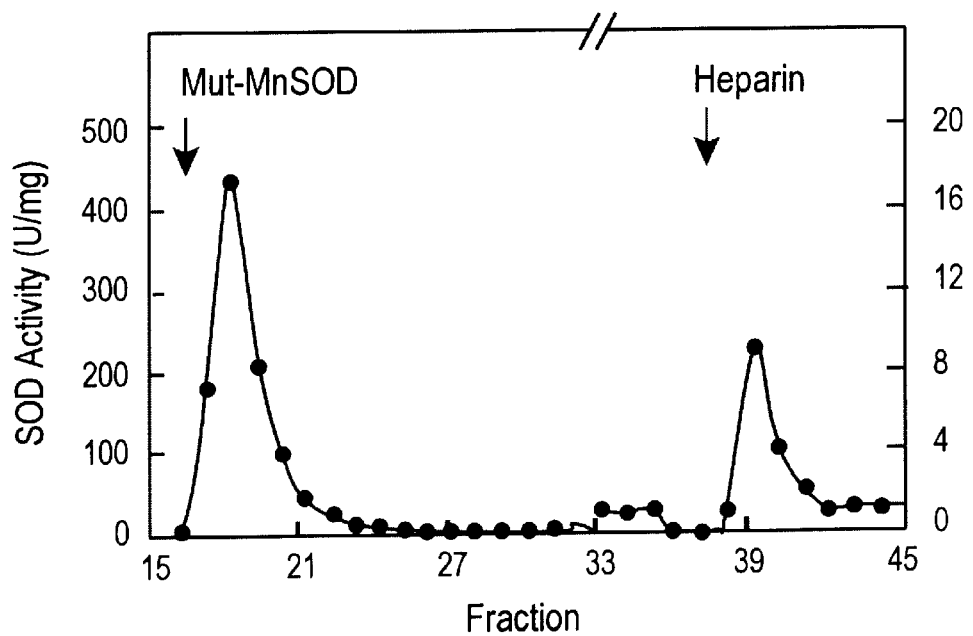
FIG. 8 is a line graph illustrating the binding of mut-MnSOD to the isolated perfused rabbit heart.

Binding of Mut-MnSOD to Endothelial Cell Surfaces An isolated rabbit heart was perfused with Krebs-Henseleit buffer in Langendorff mode (Omar et al.,1991, supra). The heart was flushed with a bolus of heparin to remove any endogenous ECSOD. After additional perfusion to remove the residual heparin, a bolus dose of 2000 U of mut-MnSOD was administered, most of which passed immediately through the heart as shown in FIG. 8. Fractions of the coronary effluent were collected until the SOD content had returned to baseline. The heart was once again perfused with a bolus of 100 U of heparin and about 15 U of mut-MnSOD activity was immediately displaced into the coronary effluent, representing the amount of mut-MnSOD that had bound to the endothelium of the heart. Native SOD, on the other hand, was completely washed out in the perfusate and none remained to be displaced by the bolus dose of heparin (data not shown).

Example 4

The following example demonstrates that in an established model of no-flow ischemia (isolated perfused Langendorff heart preparation) followed by reperfusion of the isolated rabbit heart, the mut-MnSOD was as protective as native MnSOD or Cu,ZnSOD, but at doses nearly two orders of magnitude lower.

For these experiments, New Zealand white rabbits (2–3 kg) were sacrificed with 60 mg/kg sodium pentobarbital. The hearts and lungs were quickly excised and mounted via the ascending aorta on a non-recirculating perfusion apparatus, and retrograde aortic perfusion under gravity at 80 mmHg with modified, oxygenated, glucose-containing Krebs-Henseleit buffer was initiated. The Krebs-Henseleit buffer employed was composed of (in mM): NaCl, 118; $NAHCO_3$, 24.8; KCl, 4.7; $KH_2PO_4$, 1.2; $CaCl_2$, 2.5; $MgSO_4$, 1.2; and glucose, 10. Buffers were bubbled continuously with a mixture of 95% 0, and 5% $CO_2$. The $CO_2$ helped maintain the buffers at a physiological pH of 7.4. The apparatus had extensive water jacketing connected to a water heater which maintained the buffers and the hearts at 37° C. All buffers were filtered through a Gelman GA-4, 0.8 micron Metrical membrane before use. The buffer also contained either native human recombinant Cu,ZnSOD, native human recombinant MnSOD, or the recombinant mut-MnSOD of the present invention at the indicated concentrations (FIG. 9A), which ranged from 100 U/L to 100,000 U/L. A saline-fillec latex balloon connected through a pressure transducer to a polygraph recorder (Grass Instruments Co., MA) was inserted into the left ventricle through a left atriotomy and secured by a suture to the mitral annulus. The suture was loose enough to allow fluid drainage from the ventricle. The hearts were not paced. After a 15 minute equilibration period, the developed pressure was measured, the balloon was deflated, and the hearts were subjected to 90 minutes global ischemia. This was followed by 60 minutes of reperfusion, after which the developed pressure was measured again.

Figure 9A:
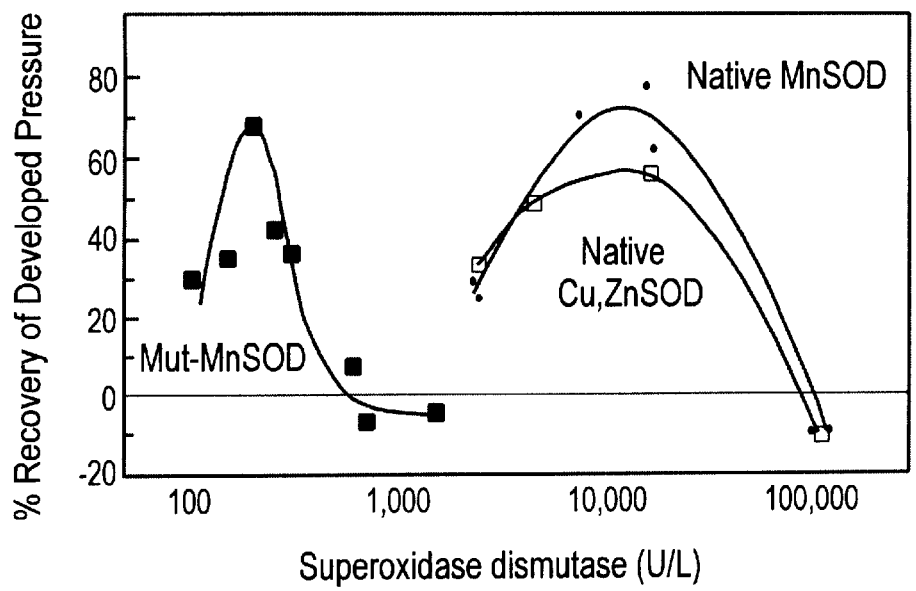
FIG. 9A is a line graph showing the protection of isolated perfused rabbit hearts from reperfusion injury by the addition of various SOD preparations to the perfusion buffer.

FIG. 9A shows the effects of the indicated concentrations of the various SOD preparations on percent recovery of preischemic developed tension. Percent protection is calculated relative to preischemic developed tension, with each heart serving as its own control. Each point represents the mean of three or more hearts. The two native enzyme preparations showed remarkably similar behavior, each providing maximal protection to the hearts at a concentration of 15,000 U/L. The mut-MnSOD, however, provided its maximal protection at a concentration of only 200 U/L. This is 75-fold more efficacious than either of the native enzymes. The results are expressed in FIG. 9A as percent recovery of the developed pressure. Bell-shaped dose response curves were observed for all SOD preparations, as was previously described (Omar et al., 1990, *Free Radical Biol. Med.* 9:473–478; and Omar et al., 1990, *Free Radical Biol. Med.* 9:465–471).

Further experiments with end-points of free radical-mediated injury confirmed the above conclusions. In these experiments, the hearts were homogenized in a buffer (1 g/4 ml) containing (in mM) HEPES, 10; NaCl, 137; KCl, 4.6; $KH_2PO_4$, 1.1; $MgSO_4$, 0.6; EDTA, 1.1; Tween-20 (5 mg/l); butylated hydroxytoluene (1 $\mu$M); and protease inhibitors (in $\mu$g/ml) leupeptin, 0.5; pepstatin, 0.7; phenyl methyl sulphonyl fluoride, 40; and aprotinin, 0.5 to prevent proteolysis of oxidized proteins during preparation. The homogenates were centrifuged at 20,000 g for 20 min. Supernates were used for carbonyl protein determinations and for analysis of thiobarbituric acid reactive substance.

Protein carbonyl groups were determined by the method of Oliver et al., 1990, *Proc. Natl. Acad. Sci. USA* 87:5144–5147, which is incorporated herein by reference in its entirety. Supernatant fractions were divided into two equal aliquots containing approximately 0.7–1.0 mg of protein each. Both aliquots were precipitated with 10% trichloroacetic acid (TCA) (w/v, final concentration). Samples were then centrifuged at 2000g for 10 min. One pellet treated with 2 N HCl and the other treated with an equal volume of 0.2% (w/v) dinitrophenyl hydrazine (DNPH) in 2 N HCl, at room temperature for 1 hour. Samples were then reprecipitated with 10% TCA (final concentration) and subsequently extracted with ethanol:ethyl acetate (1:1, v/v) and then reprecipitated with 10% TCA. This washing step, repeated 3 times, rendered the ethanol/ethyl acetate extract virtually colorless, indicating complete removal of unreacted and lipid-bound DNPH. Difference in absorbance between DNPH-treated vs the HCl control was determined at 370 nm. Data were expressed as nmol carbonyl groups/mg protein using the molar extinction coefficient of 21,000 for DNPH derivatives.

Thiobarbituric acid reactive substances, or TBARS, were deter-mined by the method of Ohkawa et al., 1979, *Anal. Biochem.* 95:351–358, which is incorporated herein by reference in its entirety. The reaction mixture (total volume of 4 ml) contained 200 $\mu$l of 8.1% sodium dodecyl sulfate, 1.5 ml of 20% acetic acid and 1.5 ml 0.8% thiobarbituric acid, and 800 $\mu$l of heart homogenate supernate. The mixture was heated in boiling water for 1 hr, cooled with tap water and extracted with n-butanol/pyridine (15:1 v/v) by vortexing for 1–2 min.

The mixture was then centrifuged at 500–1000 g for 10 minutes or until a good aqueous-organic phase separation occurred. The organic phase was removed and its absorbance at 532 nm was measured against a reaction mixture blank. A standard curve was prepared with 1,1,3,3-tetramethoxypropane, and TBARS are reported as molar equivalents.

Lactate dehydrogenase (LDH) was assayed by monitoring the rate of oxidation of NADH according to Sigma procedure #340-UV (Sigma Chemicals, St. Louis, Mo.).

Figure 9B:
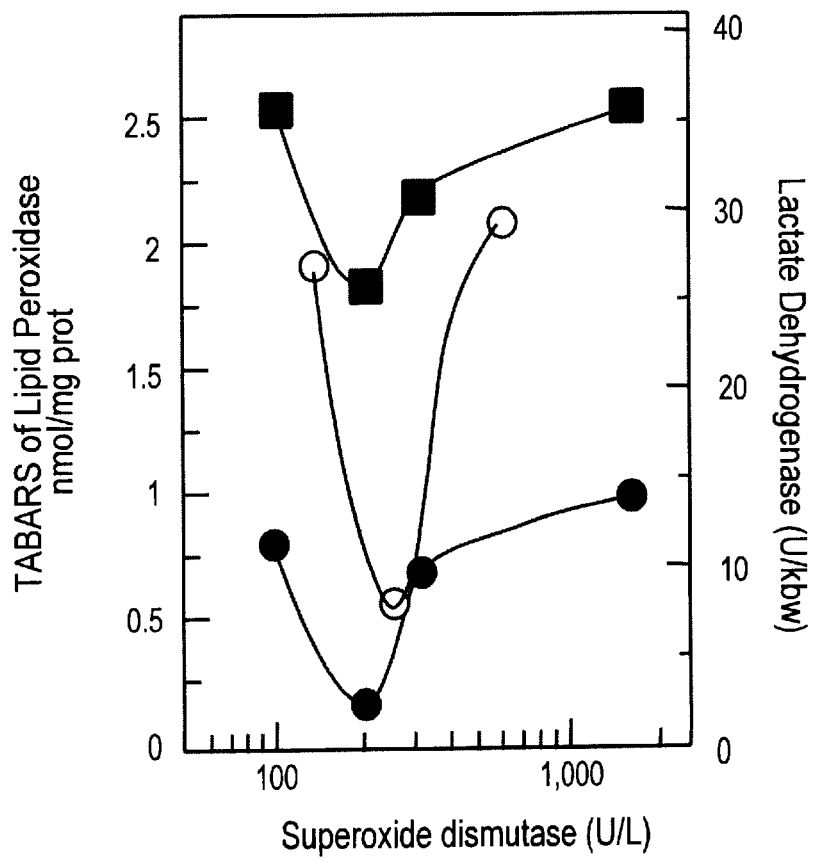
FIG. 9B is a line graph illustrating the indices of oxidative injury in the reperfused heart protected by mut-MnSOD.

Thiobarbituric acid reactive substance (●), lipid peroxides (○), and lactate dehydrogenase (■) were measured following the 90 minutes of ischemia and 30 minutes of reperfusion as shown above. FIG. 9B shows the indices of oxidative injury in the reperfused heart. These end-points were minimal in the 200–250 U/ml range of mutant MnSOD. Thiobarbituric acid reactive substances (TBARS) in the membrane fraction of the reperfused hearts showed a minimum at 200 U/ml. Lipid peroxide accumulation in the membrane fraction was determined by the xylenol orange method (Jiang et al., 1992, *Anal. Biochem.* 202:384–389, which is incorporated herein by reference in its entirety) and showed a minimum at 250 U/ml. Lactate dehydrogenase release was minimal at 200 U/ml.

Example 5

The following example demonstrates that in a rabbit heart preservation model, the mut-MnSOD provided better recovery of function after 4 hours of cold ischemia than did University of Wisconsin cardioplegia solution.

For these experiments, New Zealand white rabbits (2–3 kg) were sacrificed with 50 mg/kg sodium pentobarbital. The hearts were quickly excised and perfused via the aorta with approximately 30 ml of cold Krebs-Henseleit buffer (with or without 275 U/L of mut-MnSOD) or with University of Wisconsin cardioplegia solution (Aziz et al., 1994, *J. Heart Lung Transplant.* 13:1099–1108). The hearts were then incubated in their respective solutions for 4 hours at 4° C. At the end of the incubation period, hearts were mounted via the ascending aorta on a nonrecirculating perfusion apparatus as described above and perfused retrograde at 37° C. under gravity at 80 mmHg with modified, oxygenated, glucose-containing Krebs-Henseleit buffer (Langendorff mode). After a 60 minute recovery period, developed pressures were recorded as above.

Figure 10:
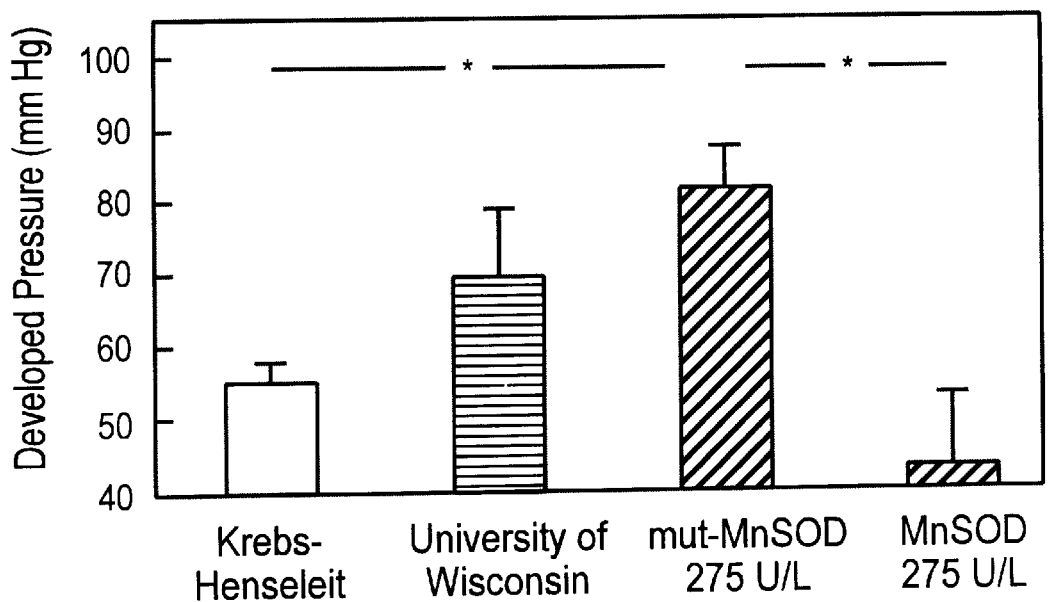
FIG. 10 is a bar graph showing protection of isolated rabbit hearts during 4 hours of cold ischemia by various cardioplegic solutions.

FIG. 10 compares the degrees of functional recovery of hearts preserved with Krebs-Henseleit buffer alone, with University of Wisconsin cardioplegia solution, with Krebs-Henseleit buffer containing 275 U/L of mut-MnSOD, or with Krebs-Henseleit buffer containing 275 U/L of native human MnSOD. Performance was measured as developed pressure. The greatest recovery occurred in hearts preserved with the mut-Mn SOD (about 82 mmHg). University of Wisconsin solution allowed developed pressures averaging 70 mmHg. Hearts stored in Krebs-Henseleit buffer returned with about 55 mmHg. Krebs-Henseleit buffer containing native human MnSOD developed about 43 mmHg pressure, not significantly different from buffer alone.

Example 6

The following experiment demonstrates that, when tested at equal doses in a model of acute lung injury induced by intratracheal instillation of IL-1, mut-MnSOD, native MnSOD and denatured mut-MnSOD showed 92%, 13.8% and 0% protection from the damage, respectively.

As a physiological model of pulmonary inflammatory injury, intratracheal IL-1 instillation followed by measurements of either lung leak or neutrophil infiltration was evaluated. In these experiments, rats were anesthetized with halothane via inhalation inside of a sealed glass jar. SODs or vehicle controls were administered at indicated doses in 0.5 ml of sterile saline via the femoral vein (See FIGS. 12 and 13). Immediately following intravenous (i.v.) injection, the trachea was cannulated with a 24-gauge, ½ inch teflon catheter and 50 ng IL-1 in 0.5 ml sterile endotoxin-free saline was rapidly instilled intratracheally with a syringe and then followed by three 1 ml injections of air. Rats were then allowed to fully recover from anesthesia. Sham-treated rats received identical anesthesia and surgery but were injected only with sterile saline both intravenously and intratracheally.

First, the ability of the mut-MnSOD to provide protection in a model of acute lung injury in vivo was tested. Four and one-half hours after SODs and IL-1 administration, rats were injected intravenously with 1.0 $\mu$Ci of $^{125}$I-labeled bovine serum albumin in a volume of 0.5 ml. Twenty minutes later, rats were ventilated using a Harvard small animal respirator and then subjected to laparotomy, thoracotomy, and right ventricular injection of 200 U of heparin in 0.2 ml of saline. Thirty minutes after $^{125}$I injection, blood samples were obtained, lungs were perfused blood-free with phosphate buffered-saline, and lungs were excised. Right lungs and blood samples were counted in a gamma counter (Beckman, Fullerton, Calif.). Lung leak index was defined as counts per minute of $^{125}$I in the right lung divided by counts per minute in 1.0 ml of blood.

Figure 11:
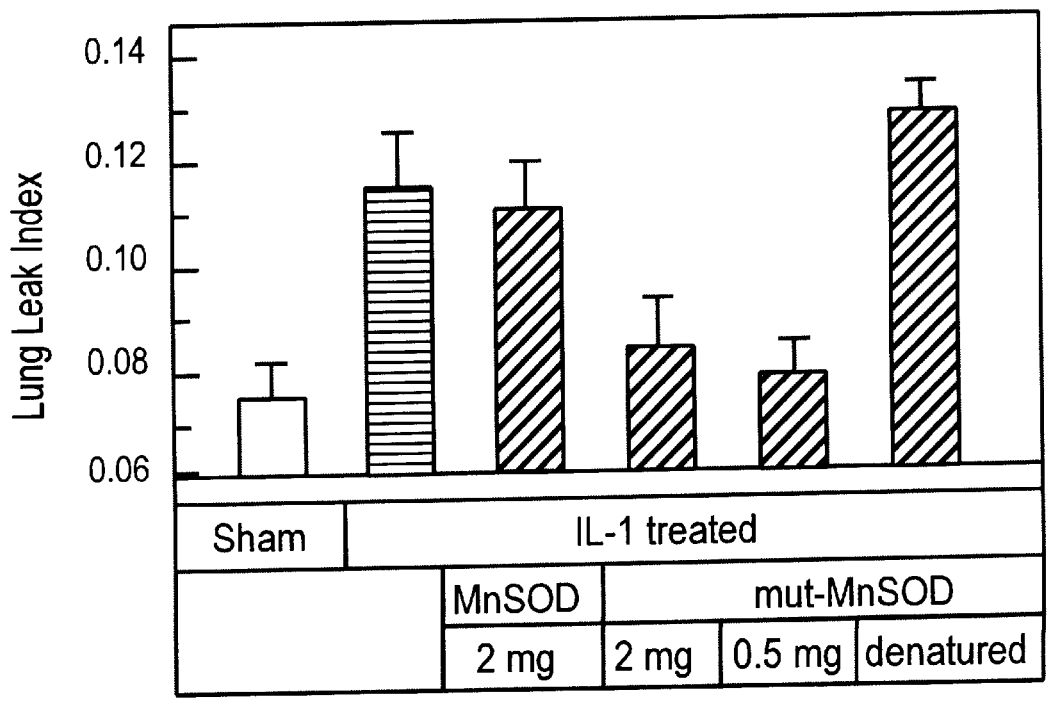
FIG. 11 is a bar graph showing protection by mut-MnSOD against IL-1-induced lung leaks in rats.

The results are shown in FIG. 11 (Group 1, sham treated rats (no IL-1); Group 2, IL-1 treated rats; Group 3, IL-1 treated rats pretreated with 2 mg native MnSOD; Group 4, IL-1 treated rats pretreated with 2 mg mut-MnSOD; Group 5, IL-1 treated rats pretreated with 0.5 mg mut-MnSOD; and Group 6, IL-1 treated rats pretreated with 2 mg heat-denatured mut-MnSOD). At 0.5 mg, the mutant MnSOD enzyme suppressed the IL-1-induced lung leak by approximately 92% (P<0.026) when compared to the IL-1 treated control. In contrast, the protection observed by 2 mg of native MnSOD treatment was only 13.8%. Denatured mutant SOD did not protect at all. Mutant SOD at 2 mg also protected against the damage (79%, P<0.03). Therefore, mut-MnSOD protects against IL-1 induced lung leak in rats.

As an additional index of injury, PMN's were measured in bronchoalveolar lavage (BAL) fluid after the SOD treatments. Saline (3 ml×2) was slowly injected intratracheally and then withdrawn. Recovered lavage fluid was centrifuged for 5 min. The supernatant was carefully removed and saved. The pellet was then resuspended in 4.0 ml water and mixed for 30 seconds to lyse erythrocytes. Immediately thereafter, 2.0 ml of 4×Ca$^{++}$Mg$^{++}$-free Hanks solution was added and mixed for 5 seconds. The new mixture was centrifuged again for 5 minutes and the supernatant discarded. The pellet was then resuspended in 1.0 ml of lavage supernatant. Total leukocytes were counted in a hemocytometer and a cytospin preparation was Wright stained to determine the percentage of neutrophils.

Figure 12:
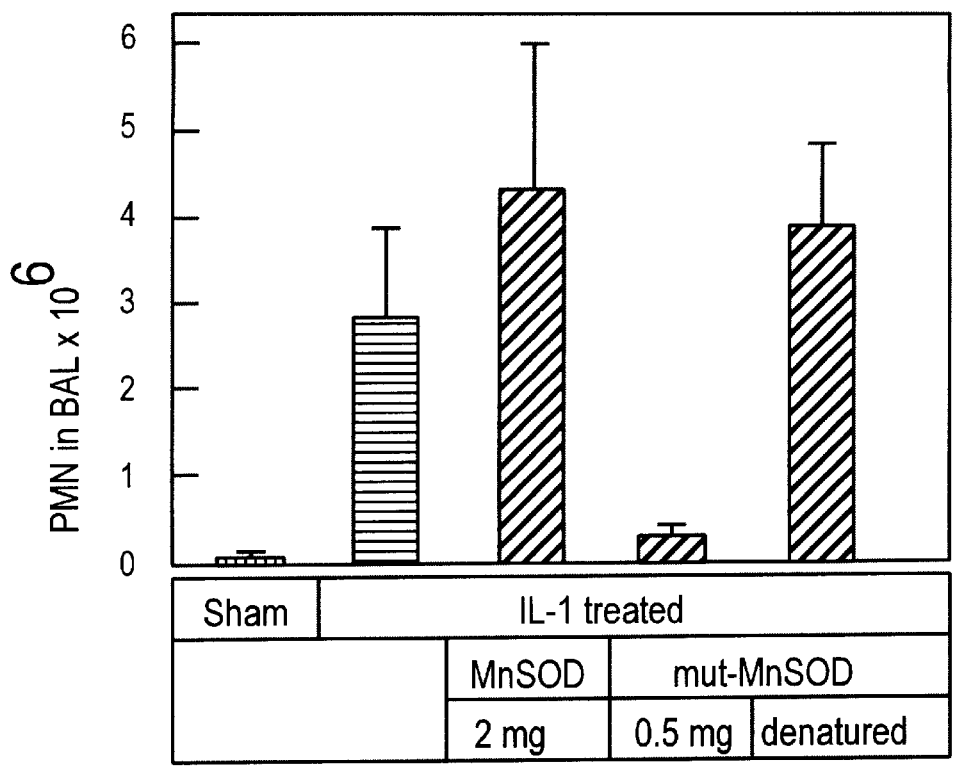
FIG. 12 is a bar graph showing prevention of PMN accumulation in IL-1 treated rat lung by mut-MnSOD.

The results are shown in FIG. 12 (Group 1 sham treated animals (no IL-1); Group 2, IL-1 treated animals; Group 3, IL-1 treated animals pretreated with 2 mg native MnSOD; Group 4, IL-1 treated animals pretreated with 0.5 mg mut-MnSOD; and Group 5, IL-1 treated animals pretreated with 2 mg heat-denatured mut-MnSOD). IL-1 administration increased the PMN in BAL. While neither native MnSOD nor denatured mut-MnSOD prevented this increase, 0.5 mg of mut-MnSOD prevented neutrophil accumulation by 91% (p<0.05). Therefore, mut-MnSOD prevents PMN accumulation in the IL-1 treated rat lung.

Figure 13:
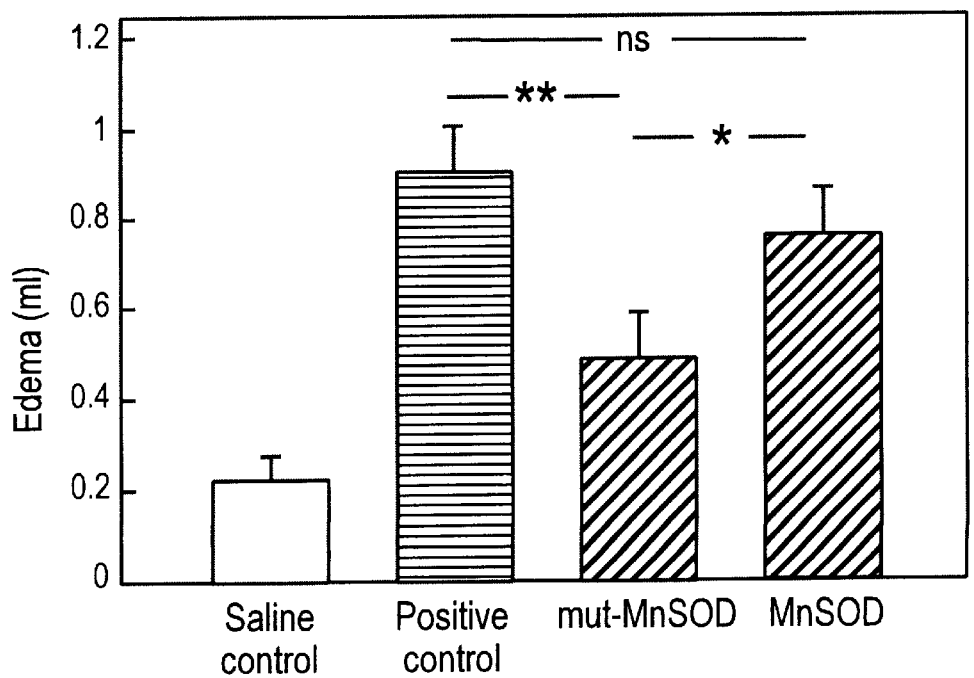
FIG. 13 is a bar graph illustrating inhibition of carrageenan-induced foot edema in the rat by native MnSOD and mut-MnSOD.

In summary, FIGS. 12 and 13 demonstrate that Mut-MnSOD prevented both neutrophil migration and the lung leak caused by the IL-1. Neither native SOD nor denatured mutant SOD protected (FIGS. 12 and 13). The only structural difference between the mutant and the native enzymes is the presence of the heparin binding "tail". Thus, we can conclude that the ability to bind to endothelial cell surfaces provides an advantage in protecting against IL-1 induced lung damage.

Example 7

The following example demonstrates that in carrageenan-induced foot edema, a standard neutrophil-mediated inflammation model of the pharmaceutical industry, the mut-MnSOD of the present invention caused substantial inhibition of edema formation at a remarkably low dose.

In these experiments, edema was induced by injection of 0.1 ml of 1.5% carrageenan in saline into the foot pad. The increase in foot volume was measured after 6 hours by water displacement. The saline controls received an injection of vehicle only. Native recombinant human MnSOD or mut-MnSOD, where indicated (FIG. 13), was administered 10 minutes prior to carrageenan by intravenous (i.v.) injection at doses of 0.1 U/g body wt.

FIG. 13 shows the increase in foot volume (+SEM) after 6 hours as measured by water displacement (Bars indicate mean+SEM. Statistical significance: ns=not significant; *: p<0.05; **: p<0.003). The saline controls (n=3), injected with vehicle only, produced 0.22±0.05 ml of edema. The carrageenan controls (n=15) produced 0.91±0.09 ml of edema. The native MnSOD reduced edema to 0.77±0.10 ml (n=8), i.e., a 20% (n.s.) reduction in carrageenan-dependent edema. The mut-MnSOD (n=9), however, reduced carrageenan dependent edema by 62% (p<0.003), to 0.48±0.11 ml.

In this model of carrageenan-induced foot edema in the rat, the mut-MnSOD provided a 62% inhibition of edema formation (p<0.003) after i.v. administration of only 0.1 U/gbw 10 minutes prior to carrageenan injection. This dosage is the equivalent of only about 2 mg for a 70 kg man. At the same dosage, native MnSOD did not produce statistically significant inhibition of edema formation. Thus, this mut-MnSOD is able to bind to cell surfaces and may aid in the prevention of superoxide-mediated endothelial damage and function as a rational therapeutic agent for the treatment of free-radical mediated diseases.

In summary, in every model examined, including both ischemia/reperfusion and inflammatory models, the mut-MnSOD provided significantly and often dramatically better protection than did native MnSOD. Based on comparisons from the literature, it appears to provide better protection than native human ECSOD or other genetically-engineered mimics of ECSOD. Hearts were protected against both warm ischemia (in a model of myocardial infarction, FIGS. 9A and 9B) and cold ischemia (in a model of organ transplantation, FIG. 10).

Example 8

The following example shows a comparison of calculated net charge values a pH 7.4 for various SODs.

Figure 14:
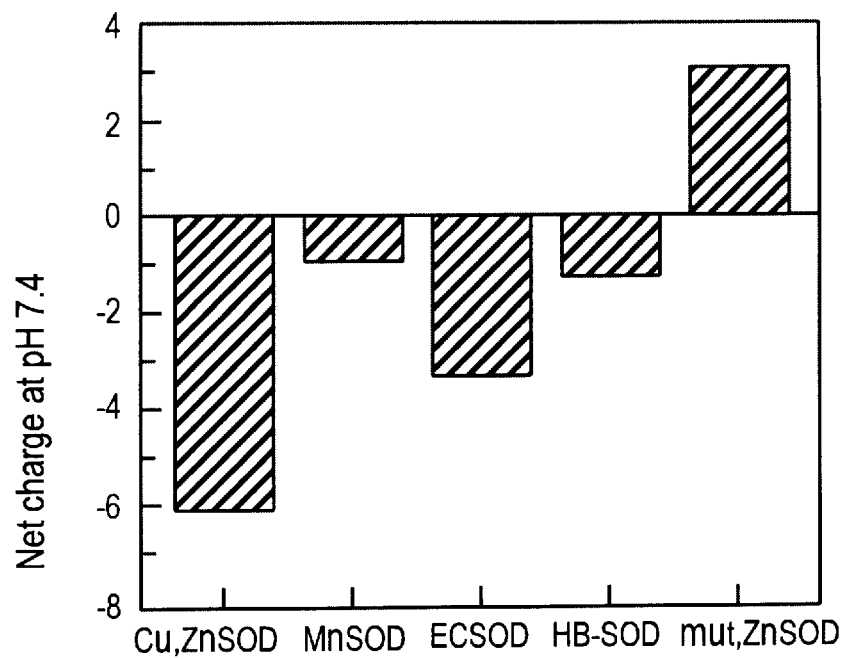
FIG. 14 is a bar graph showing calculated net charge values at pH 7.4 for three wild-type human SODs and for two heparin-binding, genetically engineered SODs.

Previously, the present inventors have shown that maintaining a proper dose is critical due to bell-shaped dose-response curves (Omar et al., 1990, supra, and Omar et al., 1990, supra) resulting from the fact that superoxide radical can paradoxically both initiate and terminate lipid peroxidation. In addition, it has been shown that the negatively charged human Cu,ZnSOD (net charge −6.1) equilibrates rather slowly between vascular and interstitial spaces, whereas the near neutrally charged MnSOD (net charge −0.85) equilibrates much more quickly (Omar et al., 1991, supra). A comparison of net charges borne by the three wild type human SODs and for two heparin-binding mutant SODS at pH 7.4 is shown in FIG. 14. Calculations were made using PC Gene software and the sequence data for the various proteins. HB-SOD consists of human Cu,ZnSOD plus the 26 C-terminal residues of EC-SOD as described by Inoue et al. (1990, supra). The native Cu,ZnSOD has a plasma half life of only around 10 minutes due to rapid renal clearance (Bayati et al., 1988, *Acta Physiol.Scand.*, 134:65–74), whereas the MnSOD has a half life of 4 to 20 hours, depending on species, and the ECSOD has a slow clearance, with a half life of about 10 hours in the rabbit (Karlsson et al., 1988, *J. Clin. Invest.* 82:762–766).

Example 9

The following example demonstrates the time course for the appearance of various SOD activity in the interstitial space of an isolated rabbit heart relative to that being perfused through the vascular compartment.

In vivo, the outcome of free radical-mediated tissue injury depends upon the concentration of the radical as well as its site of generation. Thus, exogenously added SOD which is also targeted to a particular cellular compartment would be the treatment of choice. In ischemia/reperfusion injury, damage occurs throughout both vascular and interstitial spaces. An endothelial-binding SOD would certainly protect the cells against surface-directed damage. By the same token, an SOD which equilibrates very quickly between vascular and interstitial spaces would also protect that compartment from the injury. Work by several investigators suggests that the combination of size and charge determine an enzyme's plasma half-life as well as its ability to equilibrate between vascular and interstitial spaces (Arturson et al., 1971, *Clin. Sci.* 40:137–158; Miller et al., 1985, *Experimental biology of the lymphatic circulation.* Elsevier Science Publishers, B. V., pp. 231–260; and Parker et al., 1985, *J. Appl. Physiol.* 59(4):1128–1136). The native human MnSOD has advantages over the Cu,ZnSOD in both regards: 1) MnSOD has a longer circulating half-life than the native Cu,ZnSOD (4 h vs. 7 min) (Baret et al., 1984, *Biochem. Pharmacol.* 33:2755–2760), and 2) the present inventors have found that it equilibrates four times faster between plasma and lymph (Omar et al., 1991, supra and see FIG. 15), despite its large molecular size of 89 kDa vs 32 kDa. FIG. 15 shows the time course for the appearance of SOD activity in the interstitial space of an isolated rabbit heart relative to that being perfused through the vascular compartment. Panel (a) shows human recombinant MnSOD (net charge –1) and human recombinant Cu,ZnSOD (net charge –6). Panel (b) shows bovine Cu,ZnSOD (net charge –3.0) and sharp Cu,ZnSOD (net charge –5).

There is the possibility that very tight binding of SOD to the cell surfaces would essentially sequester the bound enzyme in the vasculature and prevent its rapid equilibration to other tissue sites. Marklund and coworkers (Karlsson et al., 1993, *Free Radical Biol. Med.* 14:185–190) showed that ECSOD variants displaying lower heparin affinities equilibrated faster to the kidney vasculature than native ECSOD-C, and might enjoy a therapeutic advantage. When bound to a heparin agarose column, mut-MnSOD elutes at a lower salt concentration (0.35 M) than ECSOD-C (0.55 M) (See FIG. 7) and may therefore have an equilibration advantage. In its high affinity heparin-binding form, ECSOD has a circulating plasma half-life of about 20 hours. In contrast, the soluble ECSOD-A has a plasma half-life of 5 hours, which is similar to the plasma half-life of the native MnSOD. Thus, proteolytic treatment of either ECSOD or mut-MnSOD would release a circulating form of the enzyme, which in the case of MnSOD is known to quickly equilibrate with the interstitial spaces, protecting that compartment against injury.

SEQUENCE LISTING (1) GENERAL INFORMATION:

(iii) NUMBER OF SEQUENCES: 12

(2) INFORMATION FOR SEQ ID NO:1:

(i) SEQUENCE CHARACTERISTICS:
      (A) LENGTH: 594 base pairs
      (B) TYPE: nucleic acid
      (C) STRANDEDNESS: single
      (D) TOPOLOGY: linear (ii) MOLECULE TYPE: cDNA (ix) FEATURE:
      (A) NAME/KEY: CDS
      (B) LOCATION: 1..594

(xi) SEQUENCE DESCRIPTION: SEQ ID NO:1:

```
AAG CAC AGC CTC CCC GAC CTG CCC TAC GAC TAC GGC GCC CTG GAA CCT      48
Lys His Ser Leu Pro Asp Leu Pro Tyr Asp Tyr Gly Ala Leu Glu Pro
 1               5                  10                  15

CAC ATC AAC GCG CAG ATC ATG CAG CTG CAC CAC AGC AAG CAC CAC GCG      96
His Ile Asn Ala Gln Ile Met Gln Leu His His Ser Lys His His Ala
                20                  25                  30

GCC TAC GTG AAC AAC CTG AAC GTC ACC GAG GAG AAG TAC CAG GAG GCG     144
Ala Tyr Val Asn Asn Leu Asn Val Thr Glu Glu Lys Tyr Gln Glu Ala
            35                  40                  45

TTG GCC AAG GGA GAT GTT ACA GCC CAG ACA GCT CTT CAG CCT GCA CTG     192
```

```
Leu Ala Lys Gly Asp Val Thr Ala Gln Thr Ala Leu Gln Pro Ala Leu
         50                  55                  60

AAG TTC AAT GGT GGT GGT CAT ATC AAT CAT AGC ATT TTC TGG ACA AAC          240
Lys Phe Asn Gly Gly Gly His Ile Asn His Ser Ile Phe Trp Thr Asn
 65                  70                  75                  80

CTC AGC CCT AAC GGT GGT GGA GAA CCC AAA GGG GAG TTG CTG GAA GCC          288
Leu Ser Pro Asn Gly Gly Gly Glu Pro Lys Gly Glu Leu Leu Glu Ala
                     85                  90                  95

ATC AAA CGT GAC TTT GGT TCC TTT GAC AAG TTT AAG GAG AAG CTG ACG          336
Ile Lys Arg Asp Phe Gly Ser Phe Asp Lys Phe Lys Glu Lys Leu Thr
                    100                 105                 110

GCT GCA TCT GTT GGT GTC CAA GGC TCA GGT TGG GGT TGG CTT GGT TTC          384
Ala Ala Ser Val Gly Val Gln Gly Ser Gly Trp Gly Trp Leu Gly Phe
                115                 120                 125

AAT AAG GAA CGG GGA CAC TTA CAA ATT GCT GCT TGT CCA AAT CAG GAT          432
Asn Lys Glu Arg Gly His Leu Gln Ile Ala Ala Cys Pro Asn Gln Asp
130                 135                 140

CCA CTG CAA GGA ACA ACA GGC CTT ATT CCA CTG CTG GGG ATT GAT GTG          480
Pro Leu Gln Gly Thr Thr Gly Leu Ile Pro Leu Leu Gly Ile Asp Val
145                 150                 155                 160

TGG GAG CAC GCT TAC TAC CTT CAG TAT AAA AAT GTC AGG CCT GAT TAT          528
Trp Glu His Ala Tyr Tyr Leu Gln Tyr Lys Asn Val Arg Pro Asp Tyr
                165                 170                 175

CTA AAA GCT ATT TGG AAT GTA ATC AAC TGG GAG AAT GTA ACT GAA AGA          576
Leu Lys Ala Ile Trp Asn Val Ile Asn Trp Glu Asn Val Thr Glu Arg
                180                 185                 190

TAC ATG GCT TGC AAA AAG                                                  594
Tyr Met Ala Cys Lys Lys
                195

(2) INFORMATION FOR SEQ ID NO:2:

(i) SEQUENCE CHARACTERISTICS:
        (A) LENGTH: 198 amino acids
        (B) TYPE: amino acid
        (D) TOPOLOGY: linear (ii) MOLECULE TYPE: protein (xi) SEQUENCE DESCRIPTION: SEQ ID NO:2:

Lys His Ser Leu Pro Asp Leu Pro Tyr Asp Tyr Gly Ala Leu Glu Pro
 1               5                  10                  15

His Ile Asn Ala Gln Ile Met Gln Leu His His Ser Lys His His Ala
                20                  25                  30

Ala Tyr Val Asn Asn Leu Asn Val Thr Glu Glu Lys Tyr Gln Glu Ala
            35                  40                  45

Leu Ala Lys Gly Asp Val Thr Ala Gln Thr Ala Leu Gln Pro Ala Leu
         50                  55                  60

Lys Phe Asn Gly Gly Gly His Ile Asn His Ser Ile Phe Trp Thr Asn
 65                  70                  75                  80

Leu Ser Pro Asn Gly Gly Gly Glu Pro Lys Gly Glu Leu Leu Glu Ala
                     85                  90                  95

Ile Lys Arg Asp Phe Gly Ser Phe Asp Lys Phe Lys Glu Lys Leu Thr
                    100                 105                 110

Ala Ala Ser Val Gly Val Gln Gly Ser Gly Trp Gly Trp Leu Gly Phe
                115                 120                 125

Asn Lys Glu Arg Gly His Leu Gln Ile Ala Ala Cys Pro Asn Gln Asp
130                 135                 140

Pro Leu Gln Gly Thr Thr Gly Leu Ile Pro Leu Leu Gly Ile Asp Val
```

```
                    145                 150                 155                 160
Trp Glu His Ala Tyr Tyr Leu Gln Tyr Lys Asn Val Arg Pro Asp Tyr
                165                 170                 175
Leu Lys Ala Ile Trp Asn Val Ile Asn Trp Glu Asn Val Thr Glu Arg
            180                 185                 190
Tyr Met Ala Cys Lys Lys
            195
```

(2) INFORMATION FOR SEQ ID NO:3:

(i) SEQUENCE CHARACTERISTICS:
        (A) LENGTH: 6 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO:3:

```
Arg Lys Lys Gly Arg Arg
 1               5
```

(2) INFORMATION FOR SEQ ID NO:4:

(i) SEQUENCE CHARACTERISTICS:
        (A) LENGTH: 78 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..78

(xi) SEQUENCE DESCRIPTION: SEQ ID NO:4:

```
CCC GGG CTC TGG GAG CGC CAG GCG CGG GAG CAC TCA GAG CGC AAG AAG        48
Pro Gly Leu Trp Glu Arg Gln Ala Arg Glu His Ser Glu Arg Lys Lys
 1               5                  10                  15

CGG CGG CGC GAG AGC GAG TGC AAG GCC GCC                                78
Arg Arg Arg Glu Ser Glu Cys Lys Ala Ala
             20                  25
```

(2) INFORMATION FOR SEQ ID NO:5:

(i) SEQUENCE CHARACTERISTICS:
        (A) LENGTH: 26 amino acids
        (B) TYPE: amino acid
        (D) TOPOLOGY: linear (ii) MOLECULE TYPE: protein (xi) SEQUENCE DESCRIPTION: SEQ ID NO:5:

```
Pro Gly Leu Trp Glu Arg Gln Ala Arg Glu His Ser Glu Arg Lys Lys
 1               5                  10                  15
Arg Arg Arg Glu Ser Glu Cys Lys Ala Ala
             20                  25
```

(2) INFORMATION FOR SEQ ID NO:6:

(i) SEQUENCE CHARACTERISTICS:
        (A) LENGTH: 681 base pairs
        (B) TYPE: nucleic acid
        (C) STRANDEDNESS: single
        (D) TOPOLOGY: linear (ii) MOLECULE TYPE: cDNA (ix) FEATURE:
     (A) NAME/KEY: CDS
     (B) LOCATION: 1..681

(xi) SEQUENCE DESCRIPTION: SEQ ID NO:6:

| | | | | | | | | | | | | | | | | |
|---|---|---|---|---|---|---|---|---|---|---|---|---|---|---|---|---|
| ATG | CAT | AAG | CAC | AGC | CTC | CCC | GAC | CTG | CCC | TAC | GAC | TAC | GGC | GCC | CTG | 48 |
| Met | His | Lys | His | Ser | Leu | Pro | Asp | Leu | Pro | Tyr | Asp | Tyr | Gly | Ala | Leu | |
| 1 | | | | 5 | | | | | 10 | | | | | 15 | | |
| GAA | CCT | CAC | ATC | AAC | GCG | CAG | ATC | ATG | CAG | CTG | CAC | CAC | AGC | AAG | CAC | 96 |
| Glu | Pro | His | Ile | Asn | Ala | Gln | Ile | Met | Gln | Leu | His | His | Ser | Lys | His | |
| | | | 20 | | | | | 25 | | | | | 30 | | | |
| CAC | GCG | GCC | TAC | GTG | AAC | AAC | CTG | AAC | GTC | ACC | GAG | GAG | AAG | TAC | CAG | 144 |
| His | Ala | Ala | Tyr | Val | Asn | Asn | Leu | Asn | Val | Thr | Glu | Glu | Lys | Tyr | Gln | |
| | | 35 | | | | | 40 | | | | | 45 | | | | |
| GAG | GCG | TTG | GCC | AAG | GGA | GAT | GTT | ACA | GCC | CAG | ACA | GCT | CTT | CAG | CCT | 192 |
| Glu | Ala | Leu | Ala | Lys | Gly | Asp | Val | Thr | Ala | Gln | Thr | Ala | Leu | Gln | Pro | |
| | 50 | | | | | 55 | | | | | 60 | | | | | |
| GCA | CTG | AAG | TTC | AAT | GGT | GGT | GGT | CAT | ATC | AAT | CAT | AGC | ATT | TTC | TGG | 240 |
| Ala | Leu | Lys | Phe | Asn | Gly | Gly | Gly | His | Ile | Asn | His | Ser | Ile | Phe | Trp | |
| 65 | | | | | 70 | | | | | 75 | | | | | 80 | |
| ACA | AAC | CTC | AGC | CCT | AAC | GGT | GGT | GGA | GAA | CCC | AAA | GGG | GAG | TTG | CTG | 288 |
| Thr | Asn | Leu | Ser | Pro | Asn | Gly | Gly | Gly | Glu | Pro | Lys | Gly | Glu | Leu | Leu | |
| | | | | 85 | | | | | 90 | | | | | 95 | | |
| GAA | GCC | ATC | AAA | CGT | GAC | TTT | GGT | TCC | TTT | GAC | AAG | TTT | AAG | GAG | AAG | 336 |
| Glu | Ala | Ile | Lys | Arg | Asp | Phe | Gly | Ser | Phe | Asp | Lys | Phe | Lys | Glu | Lys | |
| | | | 100 | | | | | 105 | | | | | 110 | | | |
| CTG | ACG | GCT | GCA | TCT | GTT | GGT | GTC | CAA | GGC | TCA | GGT | TGG | GGT | TGG | CTT | 384 |
| Leu | Thr | Ala | Ala | Ser | Val | Gly | Val | Gln | Gly | Ser | Gly | Trp | Gly | Trp | Leu | |
| | | 115 | | | | | 120 | | | | | 125 | | | | |
| GGT | TTC | AAT | AAG | GAA | CGG | GGA | CAC | TTA | CAA | ATT | GCT | GCT | TGT | CCA | AAT | 432 |
| Gly | Phe | Asn | Lys | Glu | Arg | Gly | His | Leu | Gln | Ile | Ala | Ala | Cys | Pro | Asn | |
| | 130 | | | | | 135 | | | | | 140 | | | | | |
| CAG | GAT | CCA | CTG | CAA | GGA | ACA | ACA | GGC | CTT | ATT | CCA | CTG | CTG | GGG | ATT | 480 |
| Gln | Asp | Pro | Leu | Gln | Gly | Thr | Thr | Gly | Leu | Ile | Pro | Leu | Leu | Gly | Ile | |
| 145 | | | | | 150 | | | | | 155 | | | | | 160 | |
| GAT | GTG | TGG | GAG | CAC | GCT | TAC | TAC | CTT | CAG | TAT | AAA | AAT | GTC | AGG | CCT | 528 |
| Asp | Val | Trp | Glu | His | Ala | Tyr | Tyr | Leu | Gln | Tyr | Lys | Asn | Val | Arg | Pro | |
| | | | | 165 | | | | | 170 | | | | | 175 | | |
| GAT | TAT | CTA | AAA | GCT | ATT | TGG | AAT | GTA | ATC | AAC | TGG | GAG | AAT | GTA | ACT | 576 |
| Asp | Tyr | Leu | Lys | Ala | Ile | Trp | Asn | Val | Ile | Asn | Trp | Glu | Asn | Val | Thr | |
| | | | 180 | | | | | 185 | | | | | 190 | | | |
| GAA | AGA | TAC | ATG | GCT | TGC | AAA | AAG | CCC | GGG | CTC | TGG | GAG | CGC | CAG | GCG | 624 |
| Glu | Arg | Tyr | Met | Ala | Cys | Lys | Lys | Pro | Gly | Leu | Trp | Glu | Arg | Gln | Ala | |
| | | 195 | | | | | 200 | | | | | 205 | | | | |
| CGG | GAG | CAC | TCA | GAG | CGC | AAG | AAG | CGG | CGG | CGC | GAG | AGC | GAG | TGC | AAG | 672 |
| Arg | Glu | His | Ser | Glu | Arg | Lys | Lys | Arg | Arg | Arg | Glu | Ser | Glu | Cys | Lys | |
| | 210 | | | | | 215 | | | | | 220 | | | | | |
| GCC | GCC | TAA | | | | | | | | | | | | | | 681 |
| Ala | Ala | * | | | | | | | | | | | | | | |
| 225 | | | | | | | | | | | | | | | | |

(2) INFORMATION FOR SEQ ID NO:7:

(i) SEQUENCE CHARACTERISTICS:
      (A) LENGTH: 226 amino acids
      (B) TYPE: amino acid
      (D) TOPOLOGY: linear (ii) MOLECULE TYPE: protein (xi) SEQUENCE DESCRIPTION: SEQ ID NO:7:

Met His Lys His Ser Leu Pro Asp Leu Pro Tyr Asp Tyr Gly Ala Leu
1               5                   10                  15

Glu Pro His Ile Asn Ala Gln Ile Met Gln Leu His His Ser Lys His
            20                  25                  30

His Ala Ala Tyr Val Asn Asn Leu Asn Val Thr Glu Glu Lys Tyr Gln
        35                  40                  45

Glu Ala Leu Ala Lys Gly Asp Val Thr Ala Gln Thr Ala Leu Gln Pro
    50                  55                  60

Ala Leu Lys Phe Asn Gly Gly His Ile Asn His Ser Ile Phe Trp
65                  70                  75                  80

Thr Asn Leu Ser Pro Asn Gly Gly Gly Glu Pro Lys Gly Glu Leu Leu
                85                  90                  95

Glu Ala Ile Lys Arg Asp Phe Gly Ser Phe Asp Lys Phe Lys Glu Lys
                100                 105                 110

Leu Thr Ala Ala Ser Val Gly Val Gln Gly Ser Gly Trp Gly Trp Leu
            115                 120                 125

Gly Phe Asn Lys Glu Arg Gly His Leu Gln Ile Ala Ala Cys Pro Asn
    130                 135                 140

Gln Asp Pro Leu Gln Gly Thr Thr Gly Leu Ile Pro Leu Leu Gly Ile
145                 150                 155                 160

Asp Val Trp Glu His Ala Tyr Tyr Leu Gln Tyr Lys Asn Val Arg Pro
                165                 170                 175

Asp Tyr Leu Lys Ala Ile Trp Asn Val Ile Asn Trp Glu Asn Val Thr
            180                 185                 190

Glu Arg Tyr Met Ala Cys Lys Lys Pro Gly Leu Trp Glu Arg Gln Ala
        195                 200                 205

Arg Glu His Ser Glu Arg Lys Lys Arg Arg Glu Ser Glu Cys Lys
    210                 215                 220

Ala Ala
225

(2) INFORMATION FOR SEQ ID NO:8:

(i) SEQUENCE CHARACTERISTICS:
        (A) LENGTH: 3789 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:8:

```
TCGCGCGTTT CGGTGATGAC GGTGAAAACC TCTGACACAT GCAGCTCCCG GAGACGGTCA    60

CAGCTTGTCT GTAAGCGGAT GCCGGGAGCA GACAAGCCCG TCAGGGCGCG TCAGCGGGTG   120

TTGGCGGGTG TCGGGCTGG CTTAACTATG CGGCATCAGA GCAGATTGTA CTGAGAGTGC    180

ACCATATGCG GTGTGAAATA CCGCACAGAT GCGTAAGGAG AAAATACCGC ATCAGGCGCC   240

ATTCGCCATT CAGGCTGCGC AACTGTTGGG AAGGGCGATC GGTGCGGGCC TCTTCGCTAT   300

TACGCCAGCT GGCGAAAGGG GGATGTGCTG CAAGGCGATT AAGTTGGGTA ACGCCAGGGT   360

TTTCCCAGTC ACGACGTTGT AAAACGACGG CCAGTGAATT CCCTCGGGCA TTTTCCTGCA   420

AAACCATACC CTTACGAAAA GTACGGCATT GATAATCATT TCAATATCA TTTAATTAAC    480

TATAATGAAC CAACTGCTTA CGCGGCATTA ACAATCGGCC GCCCGACAAT ACTGGAGATG   540

AATATGCATA AGCACAGCCT CCCCGACCTG CCCTACGACT ACGGCGCCCT GGAACCTCAC   600
```

-continued

| | |
|---|---|
| ATCAACGCGC AGATCATGCA GCTGCACCAC AGCAAGCACC ACGCGGCCTA CGTGAACAAC | 660 |
| CTGAACGTCA CCGAGGAGAA GTACCAGGAG GCGTTGGCCA AGGGAGATGT TACAGCCCAG | 720 |
| ACAGCTCTTC AGCCTGCACT GAAGTTCAAT GGTGGTGGTC ATATCAATCA TAGCATTTTC | 780 |
| TGGACAAACC TCAGCCCTAA CGGTGGTGGA GAACCCAAAG GGGAGTTGCT GGAAGCCATC | 840 |
| AAACGTGACT TTGGTTCCTT TGACAAGTTT AAGGAGAAGC TGACGGCTGC ATCTGTTGGT | 900 |
| GTCCAAGGCT CAGGTTGGGG TTGGCTTGGT TTCAATAAGG AACGGGGACA CTTACAAATT | 960 |
| GCTGCTTGTC CAAATCAGGA TCCACTGCAA GGAACAACAG GCCTTATTCC ACTGCTGGGG | 1020 |
| ATTGATGTGT GGGAGCACGC TTACTACCTT CAGTATAAAA ATGTCAGGCC TGATTATCTA | 1080 |
| AAAGCTATTT GGAATGTAAT CAACTGGGAG AATGTAACTG AAAGATACAT GGCTTGCAAA | 1140 |
| AAGCCCGGGC TCTGGGAGCG CCAGGCGCGG GAGCACTCAG AGCGCAAGAA GCGGCGGCGC | 1200 |
| GAGAGCGAGT GCAAGGCCGC CTAATGAGCT CCATTTGCCG CCTGCTGCAA TGAGGCGTAT | 1260 |
| AGGCCGCATA TCAGCTTAAA AAATGAACCA TCGCCAACGG CGGTGGTTTT TTTGTGATCA | 1320 |
| ATTTCAAAAT AAAAACAATG ATCCGAATAA AAATAAAACA GCGTTTCAAT TGATGTGGTT | 1380 |
| TTGACACTTT TATGATTAAA TGAATGTCTA TCTTCGTTTC CATCAACACT GATGCTCCAT | 1440 |
| TGAGGAATTA CGCATCAGCC CTTAAAAATA TGCCGACAGG TGATGGAAAT GCAGATAAAA | 1500 |
| CGCTCGATTG AGAAAATCCC GGGGGGATCC GTCGACCTGC AGGGCATGCA AGCTTGGCGT | 1560 |
| AATCATGGTC ATAGCTGTTT CCTGTGTGAA ATTGTTATCC GCTCACAATT CCACACAACA | 1620 |
| TACGAGCCGG AAGCATAAAG TGTAAAGCCT GGGGTGCCTA ATGAGTGAGC TAACTCACAT | 1680 |
| TAATTGCGTT GCGCTCACTG CCCGCTTTCC AGTCGGGAAA CCTGTCGTGC CAGCTGCATT | 1740 |
| AATGAATCGG CCAACGCGCG GGGAGAGGCG GTTTGCGTAT TGGGCGCTCT TCCGCTTCCT | 1800 |
| CGCTCACTGA CTCGCTGCGC TCGGTCGTTC GGCTGCGGCG AGCGGTATCA GCTCACTCAA | 1860 |
| AGGCGGTAAT ACGGTTATCC ACAGAATCAG GGGATAACGC AGGAAAGAAC ATGTGAGCAA | 1920 |
| AAGGCCAGCA AAAGGCCAGG AACCGTAAAA AGGCCGCGTT GCTGGCGTTT TTCCATAGGC | 1980 |
| TCCGCCCCCC TGACGAGCAT CACAAAAATC GACGCTCAAG TCAGAGGTGG CGAAACCCGA | 2040 |
| CAGGACTATA AAGATACCAG GCGTTTCCCC CTGGAAGCTC CCTCGTGCGC TCTCCTGTTC | 2100 |
| CGACCCTGCC GCTTACCGGA TACCTGTCCG CCTTTCTCCC TTCGGGAAGC GTGGCGCTTT | 2160 |
| CTCAATGCTC ACGCTGTAGG TATCTCAGTT CGGTGTAGGT CGTTCGCTCC AAGCTGGGCT | 2220 |
| GTGTGCACGA ACCCCCCGTT CAGCCCGACC GCTGCGCCTT ATCCGGTAAC TATCGTCTTG | 2280 |
| AGTCCAACCC GGTAAGACAC GACTTATCGC CACTGGCAGC AGCCACTGGT AACAGGATTA | 2340 |
| GCAGAGCGAG GTATGTAGGC GGTGCTACAG AGTTCTTGAA GTGGTGGCCT AACTACGGCT | 2400 |
| ACACTAGAAG GACAGTATTT GGTATCTGCG CTCTGCTGAA GCCAGTTACC TTCGGAAAAA | 2460 |
| GAGTTGGTAG CTCTTGATCC GGCAAACAAA CCACCGCTGG TAGCGGTGGT TTTTTTGTTT | 2520 |
| GCAAGCAGCA GATTACGCGC AGAAAAAAAG GATCTCAAGA AGATCCTTTG ATCTTTTCTA | 2580 |
| CGGGGTCTGA CGCTCAGTGG AACGAAAACT CACGTTAAGG GATTTTGGTC ATGAGATTAT | 2640 |
| CAAAAAGGAT CTTCACCTAG ATCCTTTTAA ATTAAAAATG AAGTTTTAAA TCAATCTAAA | 2700 |
| GTATATATGA GTAAACTTGG TCTGACAGTT ACCAATGCTT AATCAGTGAG GCACCTATCT | 2760 |
| CAGCGATCTG TCTATTTCGT TCATCCATAG TTGCCTGACT CCCCGTCGTG TAGATAACTA | 2820 |
| CGATACGGGA GGGCTTACCA TCTGGCCCCA GTGCTGCAAT GATACCGCGA GACCCACGCT | 2880 |
| CACCGGCTCC AGATTTATCA GCAATAAACC AGCCAGCCGG AAGGGCCGAG CGCAGAAGTG | 2940 |
| GTCCTGCAAC TTTATCCGCC TCCATCCAGT CTATTAATTG TTGCCGGGAA GCTAGAGTAA | 3000 |

-continued

```
GTAGTTCGCC AGTTAATAGT TTGCGCAACG TTGTTGCCAT TGCTACAGGC ATCGTGGTGT    3060

CACGCTCGTC GTTTGGTATG GCTTCATTCA GCTCCGGTTC CCAACGATCA AGGCGAGTTA    3120

CATGATCCCC CATGTTGTGC AAAAAAGCGG TTAGCTCCTT CGGTCCTCCG ATCGTTGTCA    3180

GAAGTAAGTT GGCCGCAGTG TTATCACTCA TGGTTATGGC AGCACTGCAT AATTCTCTTA    3240

CTGTCATGCC ATCCGTAAGA TGCTTTTCTG TGACTGGTGA GTACTCAACC AAGTCATTCT    3300

GAGAATAGTG TATGCGGCGA CCGAGTTGCT CTTGCCCGGC GTCAATACGG GATAATACCG    3360

CGCCACATAG CAGAACTTTA AAAGTGCTCA TCATTGGAAA ACGTTCTTCG GGGCGAAAAC    3420

TCTCAAGGAT CTTACCGCTG TTGAGATCCA GTTCGATGTA ACCCACTCGT GCACCCAACT    3480

GATCTTCAGC ATCTTTTACT TTCACCAGCG TTTCTGGGTG AGCAAAAACA GGAAGGCAAA    3540

ATGCCGCAAA AAAGGGAATA AGGGCGACAC GGAAATGTTG AATACTCATA CTCTTCCTTT    3600

TTCAATATTA TTGAAGCATT TATCAGGGTT ATTGTCTCAT GAGCGGATAC ATATTTGAAT    3660

GTATTTAGAA AAATAAACAA ATAGGGGTTC CGCGCACATT TCCCCGAAAA GTGCCACCTG    3720

ACGTCTAAGA AACCATTATT ATCATGACAT TAACCTATAA AAATAGGCGT ATCACGAGGC    3780

CCTTTCGTC                                                            3789
```

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:9:

```
GATGAATATG CATTTCGAGC TC                                               22
```

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:10:

```
AATGGAGCTC GAAATGCATA TTCATCTC                                         28
```

(2) INFORMATION FOR SEQ ID NO:11:

(i) SEQUENCE CHARACTERISTICS:
        (A) LENGTH: 31 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "primer"

(xi) SEQUENCE DESCRIPTION: SEQ ID NO:11:

```
GGAATTCATG CATAAGCACA GCCTCCCCGA C                                     31
```

(2) INFORMATION FOR SEQ ID NO:12:

-continued

```
(i) SEQUENCE CHARACTERISTICS:
     (A) LENGTH: 34 base pairs
     (B) TYPE: nucleic acid
     (C) STRANDEDNESS: single
     (D) TOPOLOGY: linear (ii) MOLECULE TYPE: other nucleic acid
     (A) DESCRIPTION: /desc = "primer"

(xi) SEQUENCE DESCRIPTION: SEQ ID NO:12:

CGAGCTCTTA CCCGGGCTTT TTGCAAGCCA TGTA                                   34
```

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. An isolated mutant manganese superoxide dismutase protein comprising an enzymatically active portion of manganese superoxide dismutase (MnSOD) and a region which binds to polyanionic polysaccharides or proteoglycans on endothelial cell surfaces, wherein said protein is encoded by a nuclcleic acid molecule that hybridizes under conditions that achieve hyridization permitting 30% or less mismatch of nucleotides, to a nucleic acid molecule selected from the group consisting of a nucleic acid molecule comprising both nucleic acid sequences SEQ ID NO:1 and SEQ ID NO:4, a nucleic acid molecule comprising a nucleic acid sequences SEQ ID NO:6, and a nucleic acid molecule comprising a nucleic acid sequences SEQ ID NO:8, wherein said conditions comprise hybridizing in a soluition comprising 6×SSC or 6×SSPE at a temperature 20–25° C. below $T_m$, and washing at 12–20° C. below said $T_m$.

2. The isolated mutant manganese superoxide dismutase protein of claim 1, wherein said region which binds to polyanionic polysaccharides or proteoglycans is located at the C-terminus of said isolated protein.

3. The isolated protein of claim 1, wherein said nucleic acid moleculc comprises a nucleic acid sequence that encodes MnSOD.

4. The isolated protein of claim 1, wherein said nucleic acid molecule comprises a nucleic acid sequence that encodes a C-terminal region of extracelluar superoxide dismutase.

5. The isolated protein of claim 1, wherein said protein is encoded by a nucleic acid molecule selected from the group consisting of a nucleic acid molecule comprising both nucleic acid sequences SEQ ID NO:1 and SEQ ID NO:4, a nucleic acid molecule comprising a nucleic acid sequence SEQ ID NO:6, and a nucleic acid molecule comprising a nucleic acid sequence SEQ ID NO:8.

6. The isolated protein of claim 1, wherein said protein comprises an amino acid sequence selected from the group consisting of an amino acid sequence comprising both SEQ ID NO:2 and SEQ ID NO:5, an amino acid sequence comprising SEQ ID NO:7, an amino acid sequence that differs from said amino acid sequence comprising both SEQ ID NO:2 and SEQ ID NO:5 by one or a few amino acid insertions, deletions or substitutions that do not substantially affect MnSOD enzymatic activity of said isolated protein or the ability of said isolated protein to bind to polyanionic polysaccharides or proteoglycans, and an amino acid sequence that differs from said SEQ ID NO:7 by one or a few amino acid insertions, deletions or substitutions that do not substantially affect the MnSOD enzymatic activity of said isolated protein or the ability of said isolated protein to bind to polyanionic polysaccharides or proteoglycans.

7. The isolated protein of claim 1, wherein said protein comprises a fusion segment.

8. The isolated protein of claim 1, wherein said protein, when administered to a mammal, protects said mammal from oxidative damage.

9. A therapeutic composition to protect a mammal from oxidative damage, comprising:

a. a protective compound selected from the group consisting of:

(i) an isolated mutant manganese superoxide dismutase (MnSOD) protein comprising an enzymatically active portion of MnSOD and a C-termial region which binds to polyanionic polysaccharides or proteoglycans on endothelial cell surfaces, wherein said protein is encoded by a nucleic acid molecule that hybridizes under conditions that achieve hybridization permitting 30% or less mismatch of nucleotides, to a nucleic acid molemule selected from the group consisting of a nucleic acid moleculc comprising both nucleic acid sequences SEQ ID NO:1 and SEQ ID NO:4, a nucleic acid molecule comprising a nucleic acid sequence SEQ ID NO:6, and a nucleic acid molecule comprising a nucleic acid sequence SEQ ID NO:8, wherein said conditions comprise hybridzing in a solution comprising 6×SSC or 6×SSPE at a temperature 20–25° C. below $T_m$, and washing at 12–20° C. below said $T_m$; and, (ii) an isolated nucleic acid molecule comprising a nucleic acid sequence encoding said isolated mutant manganese superoxide dismutase (MnSOD) protein of (a); and, b. a pharmaceutically acceptable delivery vehicle.

10. The method of claim 9, wherein said pharmaceutically acceptable delivery vehicle is selected from the group consisting of liposomes, recombinant cells, biocompatible polymers, other polymeric matrices, capsules, microcapsules, microparticles, bolus preparations, osmotic pumps, diffusion devices, lipospheres, transdermal delivery systems, and surfactants.

11. A method to protect a mammal from oxidativc damage, comprising administering to a mammal a mutant manganese superoxide dismutase (MnSOD) protein comprising an enzymatically active portion of MnSOD and a C-terminal region which binds to polyanionic polysaccharides or proteoglycans on endothelial cell surfaces, wherein said protein is encoed by a nucleic acid motecule that hybridizes under conditions that achieve hybridization permitting 30% or less mismatch of nucleotides, to a nucleic acid molecule seleted from the group connsisting of a nucleic acid molecule comprisin both nucleic acid sequences SEQ ID NO:1 and SEQ ID NO:4, a nucleic acid molecule comprising a nucleic acid seguerce SEQ ID NO:6, and a nucleic acid molecule comprising nucleic acid sequence SEQ ID NO:8, wherein said condtions comprise hybridizing in a solution comprising 6×SSC or 6×SSPE at a temperature 20–25° C. below $T_m$, and washing at 12–20° C. below said $T_m$.

12. The method of claim 11, wherein said mammal has a condition selected from the group consisting of pulmonary inflammatory injury, lung disease, cancer, hypoxia, ischemia reperfusion injury, hyperoxia, atherosclerosis, arthritis, lupus erythematosus, hypertension, and neutrophil-mediated inflammation.

13. The method of claim 11, wherein said condition is a lung disease and said lung disease is selected from the group consisting of infant respiratory distress syndrome, adult respiratory distress syndrome, interstitial lung disease, and asthma.

14. The method of claim 11, wherein said mutant MnSOD protein is administered by at least one route selected from the group consisting of oral, nasal, intratracheal, inhaled, transdermal, rectal and parenteral routes.

15. The method of claim 11, wherein said mutant MnSOD protein is administered in a pharmaceutically acceptable delivery vehicle.

16. The method of claim 11, wherein said mutant MnSOD protein is administered in an amount that is between about 50 U/kg and about 15,000 U/kg body weight of said mammal.

17. The method of claim 11, wherein administration of said mutant MnSOD protein to said mammal results in the binding of said protein to endothelial cell surfaces in said mammal.

18. The method of claim 11, wherein administration of said mutant MnSOD protein to said mammal protects said mammal from oxidative damage.

19. The method of claim 11, wherein administration of said mutant MnSOD protein to said mammal protects said mammal from acute lung injury due to oxidative damage.

20. The method of claim 11, wherein administration of said mutant MnSOD protein to said mammal reduces neutrophil-mediated inflammation in said mammal.

21. The method of claim 11, wherein administration of said mutant MnSOD protein to organs of said mammal protects said organs from pre-transplantation and post-transplantation oxidative damage.

22. The method of claim 11, wherein said mammal is a human.

23. The isolated protein of claim 1, wherein said protein comprises an amino acid sequence selected from the group consisting of an amino acid sequence comprising both SEQ ID NO:2 and SEQ ID NO:5, and an amino acid sequence comprising SEQ ID NO:7.

* * * * *